United States Patent
Whitney et al.

(10) Patent No.: US 11,983,666 B2
(45) Date of Patent: May 14, 2024

(54) PHARMACEUTICAL PROCUREMENT AND INVENTORY MANAGEMENT

(71) Applicant: Trulla, LLC, Draper, UT (US)

(72) Inventors: Angela Whitney, Draper, UT (US); Curtis James McEntire, Draper, UT (US); John Richard Bucher, Salt Lake City, UT (US); Patrick Ryan Sims, Kearns, UT (US); Robert Al Nahoopii, Draper, UT (US); Sheldon Todd Merrill, Murray, UT (US)

(73) Assignee: Trulla, LLC

( * ) Notice: Subject to any disclaimer, the term of this patent is extended or adjusted under 35 U.S.C. 154(b) by 38 days.

(21) Appl. No.: 16/841,628

(22) Filed: Apr. 6, 2020

(65) Prior Publication Data

US 2020/0320470 A1    Oct. 8, 2020

Related U.S. Application Data

(60) Provisional application No. 62/830,143, filed on Apr. 5, 2019.

(51) Int. Cl.
*G06Q 10/087* (2023.01)
*G06F 9/54* (2006.01)
(Continued)

(52) U.S. Cl.
CPC .......... *G06Q 10/087* (2013.01); *G06F 9/547* (2013.01); *G06N 3/08* (2013.01); *G06Q 30/0201* (2013.01); *G06Q 50/22* (2013.01)

(58) Field of Classification Search
None
See application file for complete search history.

(56) References Cited

U.S. PATENT DOCUMENTS 10,685,308 B1 *  6/2020  Avery, Jr. .......... G06Q 10/06315
2010/0145506 A1 *  6/2010  Waugh .................. G16H 40/20
                                                    700/231
(Continued)

FOREIGN PATENT DOCUMENTS

AU         2016100803 A4 *  8/2016
JP          4220885 B2 *  2/2009
WO     WO-2009045899 A2 *  4/2009  .......... H04M 7/0024

OTHER PUBLICATIONS

Research on Optimization of Pooling System and Its Application in Drug Supply Chain Based on Big Data Analysis, DengFeng Wu and HongyiMao, Feb. 15, 2017, International Journal of Telemedicine and Applications, vol. 2017,, 15 pages.*

(Continued)

*Primary Examiner* — Ariel J Yu
(74) *Attorney, Agent, or Firm* — TechLaw Ventures, PLLC; Terrence J. Edwards

(57) ABSTRACT

Management of pharmaceutical procurement for a pharmaceutical ordering location. A method includes determining a medication need and a drug product preference for an ordering location. The method includes identifying one or more drug products satisfying the medication need by communicating with one or more pharmaceutical suppliers and selecting at least one of the one or more drug products based on the drug product preference. The method includes generating a recommended order for the ordering location comprising the at least one of the one or more drug products.

30 Claims, 14 Drawing Sheets

(51) Int. Cl.
   *G06N 3/08*      (2023.01)
   *G06Q 30/0201*   (2023.01)
   *G06Q 50/22*     (2018.01)

(56) References Cited

U.S. PATENT DOCUMENTS

| | | | |
|---|---|---|---|
| 2010/0161345 A1* | 6/2010 | Cain | G16H 40/20 |
| | | | 705/28 |
| 2010/0324936 A1 | 12/2010 | Vishnubhatla et al. | |
| 2011/0078057 A1 | 3/2011 | Lewis et al. | |
| 2014/0278495 A1* | 9/2014 | Rourke | G06Q 10/06315 |
| | | | 705/2 |
| 2014/0350952 A1* | 11/2014 | Utech | G16H 40/20 |
| | | | 705/2 |
| 2016/0048798 A1* | 2/2016 | Meyer | G01G 19/4144 |
| | | | 705/28 |
| 2017/0061375 A1* | 3/2017 | Laster | G16H 50/30 |
| 2018/0204176 A1 | 7/2018 | Eller | |
| 2019/0266554 A1* | 8/2019 | Lin | G06Q 30/0202 |
| 2020/0074402 A1* | 3/2020 | Adato | G06K 9/00771 |
| 2020/0299062 A1* | 9/2020 | Kazama | G06Q 10/087 |

OTHER PUBLICATIONS

Pharmaceutical supply chain specifics and inventory solutions for a hospital case, Peter Kelle, Aug. 2012, Elsevier Ltd, 10 pages.*
United States Patent and Trademark Office, "International Search Report", dated Jun. 22, 2020, International Application No. PCT/US20/26958.

* cited by examiner

PHARMACEUTICAL PROCUREMENT AND INVENTORY MANAGEMENT

CROSS-REFERENCE TO RELATED APPLICATION

This application claims the benefit of U.S. Provisional Patent Application No. 62/830,143, filed Apr. 5, 2019, titled "ORDERING SYSTEM AND METHOD," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

The disclosure relates generally to data analysis and relates particularly to pharmaceutical procurement and pharmaceutical inventory management.

BACKGROUND

Healthcare pharmaceutical procurement and inventory management can be extraordinarily complex. Health systems, healthcare facilities, and pharmacies must purchase pharmaceuticals for patient care, and the annual drug expenditure by a single health system can cost millions and sometimes billions of USD. The cost of pharmaceuticals is further impacted by the complexity of the drug purchasing process. Numerous different pharmaceutical suppliers sell the same medications, and each of the numerous suppliers may have different contractual relationships with health systems. Further, medication manufacturers and pharmaceutical companies may offer drug rebates that can lead to significant savings. However, it is impossible for an individual tasked with managing drug inventory to ensure that all medications are purchased in light of the supplier contracts and drug rebates to result in the most fiscally advantageous purchase. Additionally, sound pharmaceutical procurement practices are impacted by numerous factors that can change constantly in real-time and are impossible for a human to track.

Because pharmaceutical procurement and inventory management is so complex, and because this job is traditionally performed by individuals, health systems are spending more money than necessary on pharmaceutical inventory. In light of the foregoing, disclosed herein are systems, methods, and devices for automated pharmaceutical procurement and inventory management.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

Figure 1:
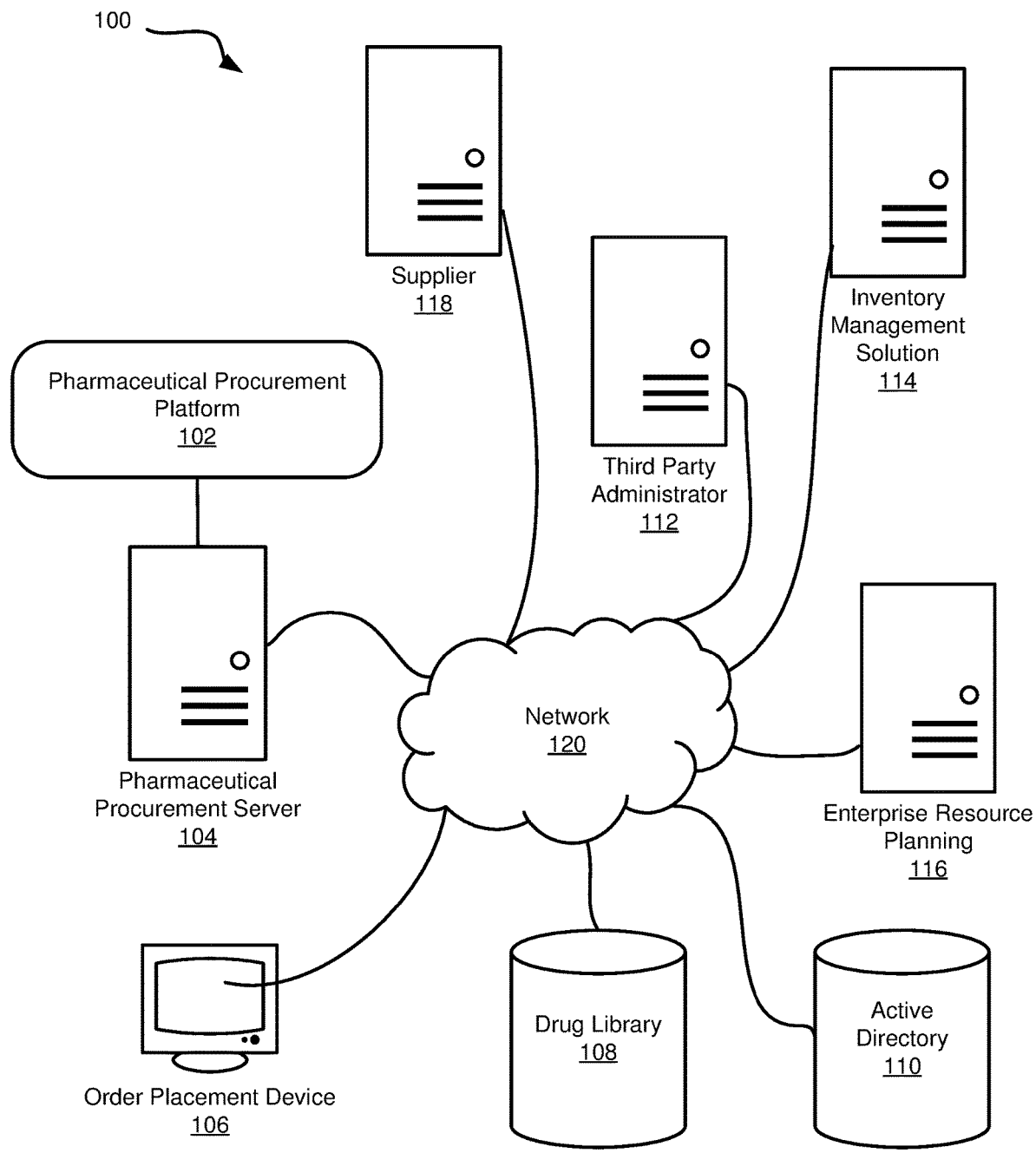
FIG. 1 is a schematic diagram of a system for pharmaceutical procurement and inventory management.

Disclosed herein are systems, methods, and devices for pharmaceutical procurement. A system of the disclosure includes a pharmaceutical procurement platform for managing pharmaceutical inventory and ordering processes. The system optimizes pharmaceutical purchasing in a compliant and cost-effective manner to ensure healthcare entities have a sufficient inventory of various medications, are purchasing the best medications for their patients, and are purchasing medications at the best prices.

An embodiment of the disclosure is a pharmaceutical procurement platform for assisting a pharmaceutical ordering location in selecting specific drug products to fulfill a medication need. The pharmaceutical procurement platform may interact with multiple outside parties to determine the best pricing and supplier for the drug products. Additionally, the pharmaceutical procurement platform may identify desirable drug products for the ordering location based on government regulations, internal strategy or business analytics for the ordering location, medication ordering permissions for the ordering location, and so forth. The pharmaceutical procurement platform simplifies the pharmaceutical purchasing process for the ordering location.

Health systems, healthcare facilities, healthcare clinics, and pharmacies must purchase pharmaceuticals to provide for patient care. A health system may include a group of healthcare practitioners, clinics, hospitals, and other facilities that are associated under a single entity. A health system may operate with a variety of professional relationships with the various entities falling under the umbrella of the health system. In some instances, the health system orders pharmaceuticals on behalf of all entities within the health system.

In some instances, one or more clinics, hospitals, facilities, or pharmacies within the health system are tasked with purchasing their own pharmaceuticals. In some instances, the health system determines protocols for purchasing pharmaceuticals, and then one or more individual entities are tasked with carrying out pharmaceutical purchase orders. Pharmaceutical pricing is exceptionally complex, and the individuals tasked with purchasing pharmaceuticals inevitably make errors when ordering drugs. These errors can be very costly and lead to increased healthcare costs.

The annual expenditure on pharmaceuticals by a single health system can cost millions and sometimes billions of USD. At a hospital, an individual tasked with purchasing pharmaceuticals (may be referred to herein as a drug buyer) is typically a pharmacy technician with limited to no formal training in drug purchasing. Typically, the drug buyer is given a generic set of instructions to ensure the hospital does not run out of any pharmaceuticals and does not spend too much money on pharmaceuticals. From there, the drug buyer typically must guess which drug products should be purchased, how much should be purchased, which supplier should be used, and so forth. The selection of a supplier may include the selection of a manufacture, wholesaler, internal/external source, and so forth. This leads to a great number of purchasing errors that can be extremely costly for the health system.

Pharmaceutical contracts are extraordinarily complex, difficult to interpret, and they can be difficult to adhere to compliantly. It can be challenging or impossible to consistently purchase pharmaceuticals in the most cost effective manner. There are many factors that should be considered when purchasing a pharmaceutical. Additionally, the makeup of the various factors is continually changing. These factors are found in disparate systems and cannot all be accessed by the individual who is tasked with processing a pharmaceutical order. The best choice for a single purchasable pharmaceutical may change several times in a year for a health system. Additionally, the best purchasing practice for a certain health system is often unique to the hospitals, clinics, and pharmacies within the health system. As a result, an individual ordering pharmaceuticals will make frequent purchasing errors that increase the overall pharmaceutical spend for the health system.

In traditional systems, the individuals tasked with purchasing pharmaceuticals (may be referred to herein as "drug product buyer," "drug buyer," "buyer," or "pharmaceutical buyer") do not have access to real-time data for all pertinent factors at the point of purchasing. For example, an individual may be tasked with purchasing pharmaceuticals for a hospital. The hospital drug buyer may have access to some information but will not have access to real-time updates to all pertinent information. Additionally, even if the hospital drug buyer had access to all information in real-time, the hospital buyer could not assimilate the extensive and extremely complex information to consistently make the best purchasing decisions.

In traditional systems, pharmaceutical buyers are tasked with personally evaluating the available information. This is a time consuming process that leads to numerous errors in pharmaceutical purchasing. After a buyer has completed an evaluation for a particular drug, the drug will continue to be purchased until that same buyer decides the purchasing protocol for that drug should be reevaluated. This often occurs months or years after the initial purchasing protocol is developed for the drug. The buyers tasked with purchasing pharmaceuticals do not routinely receive feedback on purchasing decisions and will continue to make mistakes without interruption. If purchasing mistakes are identified retrospectively, this generally occurs because the purchasing protocol was very costly to the health system. Even if a purchasing error is identified, there are no systems for enabling the health system to correct the mistake, communicate the correction to all individuals purchasing pharmaceuticals, and guide the purchasing protocol throughout the health system. Therefore, purchasing errors persist despite best efforts.

In some traditional systems, an inventory management system includes an automated dispensing system such as cabinets, carousels, robotics, virtual shelves, and so forth that manage the drug inventory at all times. An inventory management system can interface with a wholesaler and build a recommended drug order based on current inventory numbers. However, the recommended order is based on inventory quantities alone and still requires manipulation by a drug buyer and official order placement. The wholesaler may send data back after an order is placed so the drug buyers know what to expect to receive. Wholesalers interface with third-party administrators to help hospitals and clinics manage and improve compliance with government pricing programs. While this approach is functionally helpful, it is a focused approach to an issue instead of a comprehensive solution for pharmaceutical procurement.

In some instances, pharmaceutical inventory at an ordering location (e.g., a hospital or clinic) may reside in more than one system. When this is the case, some inventory might not be tracked by an inventory management system or other tracking method. This untracked inventory may then sit on a shelf, unused and contribute to misinformation applying to drug shortage calculations. In some cases, drug shortage information will be provided to pharmaceutical ordering locations through website postings, mailed notifications, emailed notification, and so forth. When the drug shortage information is conveyed by these processes, most drug product buyers will not consider this information when placing a pharmaceutical order.

Further, in some instances, drug rebate information is not available to drug product buyers and is only available to the contracting department within the health system. When this is the case, the drug product buyer for a certain ordering location within the health system will not likely purchase pharmaceuticals in a way that qualifies the ordering location to claim the drug rebate. Additionally, preferred supplier information is traditionally not available to the drug product buyer for an ordering location and must instead be remembered by the drug product buyer. Again, this leads to frequent ordering mistakes and inefficient use of funds.

The current pharmaceutical procurement process is a continuation of traditional processes that have been in place for decades. For internal orders and direct vendors (i.e., many manufacturers), many health systems still use faxes or handwritten paper orders to communicate the needs of a healthcare location. Health systems have generally moved to electronic order placement for external orders to wholesalers and many have inventory management solutions and third-party administrators. However, there is a precarious gap where one solution ends to reach the next solution which addresses a separate issue. The drug buyer's personal know-how is the only thing attempting to bridge that gap. Further, not all gaps in the pharmaceutical procurement process can be bridged by drug buyer know-how. Some data factors lay beyond the reach of the drug buyers placing orders for pharmaceuticals, such as utilization data, health system-wide data, healthcare facility-wide data, inventory numbers, nuanced details of government pricing programs, government regulations, internal strategies, formulary decisions, company policies, and so forth. Because drug buyers do not have access to this information, drug buyers will routinely place unoptimized pharmaceutical orders that are unnecessarily expensive, inaccurate, include the wrong quantity of pharmaceuticals, and so forth.

Numerous factors must be considered to make the best purchasing decision for a pharmaceutical. In some instances, it is important to consider each of the factors every time the pharmaceutical is ordered. When an individual person is making the pharmaceutical ordering decision, it is unrealistic and even impossible for the individual to consider each of the pertinent factors. Often, hundreds of thousands of unique drugs are ordered by a health system daily by numerous independent individuals. Pharmaceutical buyers have varied experience, training, and access to the information required to make the best purchasing decisions. This makes it impossible to select the ideal drug product with optimal quality, and order from the preferred supplier each time without overpaying. Costly mistakes include inadvertently purchasing a higher priced item, purchasing incorrect quantities resulting in expired medications or insufficient stock for patient care, or ordering the wrong drug product entirely.

Drug buyers are tasked with stocking pharmaceuticals for a healthcare entity such as a hospital, clinic, or pharmacy, and are expected to make smart purchasing decisions without having access to real-time information regarding the pharmaceutical industry. In traditional systems, a drug buyer for a hospital is expected to keep the hospital's pharmacy well stocked without spending too much on pharmaceuticals. The drug buyer will determine, based on his/her personal opinion, which drug products should be ordered, from which supplier the drug products should be ordered, which package sizes of drug products should be ordered, how to minimize the spend on these drug products, and so forth. The factors leading to the drug buyer's original personal decisions will continually change, and yet, the drug buyer will likely continue to purchase pharmaceutical drug products based on a purchasing protocol he/she developed months or years ago. The drug buyer does not have access to the rapidly changing data that could indicate to the drug buyer that the purchasing protocol should be amended. Drug product buyers typically perform periodic quick-checks for lower sticker prices in an attempt to manage cost. This process prevents a health system from standardizing drug products purchased and maximizing the captured savings. Generally, hospital drug buyers do not have the ability to see the drug products purchased, or the price paid by other facilities within the health system.

The pharmaceutical expenditure for a clinic is considerably less than that for a hospital. However, clinic drug product buyers typically have access to even less information and training than hospital drug product buyers. In many instances, the process of purchasing pharmaceuticals is given to a medical assistant, nurse, or administrative assistant who has other job responsibilities and does not have the bandwidth to dedicate time and resources to determining effective drug product purchasing protocols for the clinic. The clinic drug product buyer must use his/her clinical knowledge, which is typically not pharmacy-focused, to make the best guess regarding pharmaceutical purchasing.

In an embodiment, a drug product purchasing system provides information based on numerous factors. The factors may include information on the drug product itself, the strength of the drug product, and the form of the drug product, for example, whether the drug product is a tablet, injection, inhalation, ophthalmic, topical, or other drug. The factors may include information on the release mechanism for the drug product, for example, whether the drug product is immediate release, delayed release, sustained release, controlled released, or enteric coated. The factors may include information on the quantity of the drug product needed based on predetermined maximums and minimums. The factors may include information on a preferred package type for the drug product, a required package type for the drug product, and whether there are multiple possible package types for the drug product. The factors may include information on the available package sizes for the drug product, and whether there is a preferred or required package size for the drug product. The factors may include a package-type restriction indicating that the ordering location cannot use or accept a certain package and/or a package-type preference indicating that the ordering location prefers a certain package type but may accept other package types. The factors may include information on drug product shortages at the global, national, local, health system, and healthcare facility levels. The factors may include information on drug product shortage strategy implemented by the health system and/or healthcare facility. The factors may include information on allocations determined by wholesalers, manufacturers, and the health system itself. The factors may include information on inventory visibility within a healthcare department, healthcare facility, or health system. The factors may include information on drug products on formulary for the health system and/or healthcare facility. Health systems may intensively review literature, evaluate drug products for an indication, and approve a list of drug products allowed to be used within the health system based on efficacy, safety, and cost. The factors may include information related to a government pricing programs, such as the 340B Drug Pricing Program in the United States. The factors may include information on applicable local and national laws. The factors may include information on internal company policies. The factors may include information on various suppliers with unique inventory, account numbers, modes for ordering (e.g., email, phone call, online ordering portal, etc.), and availability. The factors may include information on storage and handling requirements, such as whether the drug product should be refrigerated, frozen, stored at room temperature, or stored in a safe place because the drug product is considered hazardous. The factors may include information on available storage space, including available refrigerated space, available frozen space, available room temperature space, and available hazardous-material space. The factors may include information on class of trade for various drug products.

When an individual is tasked with purchasing pharmaceuticals for a health system, hospital, clinic, pharmacy, or other facility, the individual is usually given a generic set of instructions to ensure that the entity does not run out of any drug product, and that the entity does not spend too much money on any drug product. In an embodiment, a system analyzes one or more of the aforementioned factors to enable the drug product buyer to make an educated decision to purchase the correct drug products, the correct quantity of drug products, and to ensure the healthcare entity minimizes the spend on pharmaceuticals. Each of the aforementioned factors can change frequently and can have a significant impact on whether a drug product should be purchased, how much is spent on a drug product, from which supplier the drug product should be purchased. The system provides real-time updates and guidance regarding pharmaceutical purchasing transactions that are based on real-time data that cannot be assessed by a human being.

Before the structures, systems, and methods for identifying relationships between healthcare entities are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the terms "pharmaceutical," "medication," and "drug product" may all refer to drug product(s) or classes of drug products within the pharmaceutical field. As used herein, the terms "pharmaceutical," "medication," and "drug product" may have different specific meanings for the sake of clarity, although the use of these terms should not be seen as limiting. As used herein, the term "pharmaceutical" may generally refer to policies, decisions, preferences, and products falling under the broad category of pharmaceuticals.

The term "medication" may refer to a grouping of one or more drug products. The grouping of one or more drug products is not limiting. In example embodiments discussed herein, a medication may include a grouping of pharmaceutical equivalent drug products, a grouping of therapeutic equivalent drug products, a grouping of medications and/or drug products used in a specified treatment plan, a grouping of medications and/or drug products used in a drug kit, and so forth. A medication may refer to drug products in identical or similar dosage forms and routes of administration that include identical amounts of the identical active drug ingredient. A medication may refer to drug products having the same pharmacological effects and actions in the treatment of illnesses as other drug products, even if the drug products are not chemically equivalent. A medication may refer to a collection of unique medications that are used in combination for a treatment plan or used over the course of a treatment plan. A medication may refer to a collection of unique medications within a drug product kit.

The term "drug product" may refer to a unique and identifiable pharmaceutical, such as a drug, a vitamin, a health supplement, pharmaceutical equipment, a pharmaceutical device, and so forth. In some embodiments, and particularly those embodiments implemented in the United States, the drug product may be associated with a unique National Drug Code (NDC) identifier. A drug product may be associated with a certain dosage, a certain packaging type, a certain manufacturer, a certain labeling mechanism, and so forth. A plurality of drug products may be associated with a single medication. A plurality of drug products may be pharmacologically equivalent or therapeutically equivalent.

Referring now to the figures, FIG. 1 is a schematic diagram of a system 100 for pharmaceutical procurement and streamlined pharmaceutical ordering and inventory management. The system 100 includes a pharmaceutical procurement platform 102 operated by a pharmaceutical procurement server 104. The pharmaceutical procurement server 104 is in communication with numerous other computing resources, databases, and other entities by way of a network 120 connection. The system includes an order placement device 106, such as a computer, mobile computing device, smartphone, or other device in communication with the pharmaceutical procurement platform 102 by way of the network. A user may connect to the pharmaceutical procurement platform 102 by way of the order placement device 106.

It should be appreciated that in various embodiments of the invention, the pharmaceutical procurement server 104 may be in communication with any one of the order placement device 106, drug library 108, active directory 110, third-party administrator 112, inventory management solution 114, enterprise resource planning 116, and/or supplier 118. Any of the embodiments discussed herein and illustrated in the figures may be combined or separated in various embodiments of the invention. The various components of the pharmaceutical procurement server 104, for example the components illustrated in FIG. 2, may be combined or separated in a wholistic system for pharmaceutical ordering and inventory management.

The system 100 may include a drug library 108 stored in a database in communication with the network 120. The system 100 may or may not include an active directory 110 stored in a database in communication with the network 120. The system 100 may or may not include a third-party administrator (TPA) 112 server, an inventory management solution (IMS) 114 server, a supplier 118 server, and an enterprise resource planning (ERP) 116 server in communication with the network 120. The pharmaceutical procurement server 104 analyzes and assesses information retrieved from one or more of the drug library 108, the active directory 110, the third-party administrator 112, the inventory management solution 114, the enterprise resource planning 116, and/or the supplier 118 to manage the ordering, order tracking, and inventory of a healthcare entity that procures pharmaceuticals.

Figure 3:
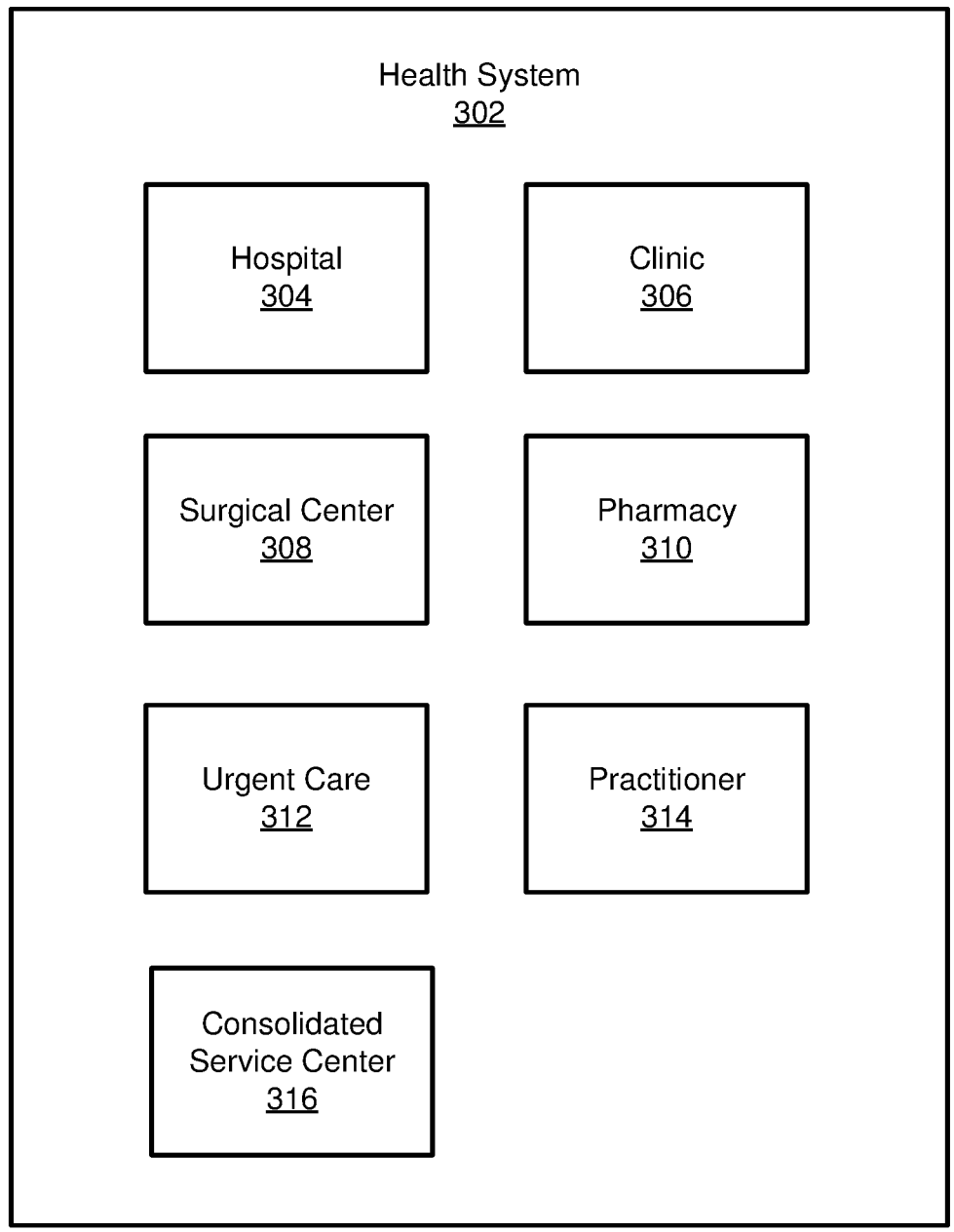
FIG. 3 is a schematic block diagram illustrating exemplary components that may fall under the umbrella of a health system.

The pharmaceutical procurement platform 102 includes a user interface and logic for managing a drug product inventory for a healthcare ordering location, such as any of the healthcare entities discussed with respect to FIG. 3. The pharmaceutical procurement platform 102 is operated by the pharmaceutical procurement server 104, which is in communication with other entities and databases by way of Application Program Interfaces (APIs), Secure File Transfer Protocols (SFTP), or other connections by way of the network 120.

The order placement device 106 is any personal computing device that can communicate with the pharmaceutical procurement server 104. The order placement device 106 may include a smart phone, a tablet, a laptop, a personal computer, and so forth. Order placement devices 106 may communicate with the pharmaceutical procurement server 104 by way of a local area network (LAN), wide area network (WAN), or another network connection. In an embodiment, order placement devices 106 can connect to a network 120, such as a cloud computing network or the Internet, by way of a network connection that may be facilitated by the pharmaceutical procurement server 104.

In an embodiment, a user accesses an account associated with the pharmaceutical procurement platform 102 by way of the order placement device 106. In an embodiment, the user is assigned a security role and location access to as many or few healthcare location as is required by the user's position. Security roles restrict what information and/or functionality the user can access. A unique ordering and/or delivery site, currently defined within the software as a location, allow users to operate within the confines of their security role at those various locations.

The drug library 108 is a repository of drug product information. In an embodiment, the drug library 108 is a digital, comprehensive drug product information resource. The pharmaceutical procurement server 104 may access the drug library 108 by way of an Application Program Interface (API) over the network 120 connection. The API allows the pharmaceutical procurement server 104 to receive automatic updates from the drug library 108 as needed. The pharmaceutical procurement server 104 extracts information from the drug library 108 for presentation with the pharmaceutical procurement platform 102 within desired data fields.

In an embodiment, the pharmaceutical procurement server 104 maintains the drug library 108. In an alternative embodiment, the drug library 108 is external to the pharmaceutical procurement server 104. The drug library 108 provides the source listing of all drug products for each health system using the pharmaceutical procurement platform 102. The server 104, with information obtained from the drug library 108, places drug products into interchangeable ordering groups.

In an embodiment, data within the drug library 108 is stored in a relational database, and a Structured Query Language (SQL) request is sent to the drug library 108 to retrieve certain information fields for medications. The information fields may include one or more of generic product identifier (GPI), medication description, brand name, size, form, controlled substance schedule, storage condition code, national drug code (NDC), manufacturer, package size and unit, package quantity, package description, and whether the medication is unit dosed. The requested fields are articulated at multiple points. This integration allows the pharmaceutical procurement server 104 to perform price conversion and package size conversion at the level of each unit according to the designation provided as to whether the supplier 118 provides medications in a full pack size or in individual units. Additionally, this enables the pharmaceutical procurement server 104 to provide users with basic and advanced data relating to selected medications without losing anything needed for various compliance points and analytics.

In an example implementation, in the United States, much of the information in the drug library 108 is obtained from the United States Food and Drug Administration (FDA). Drug products are identified and reported using a unique, three-segment number referred to as the National Drug Code (NDC). The NDC serves as a universal product identifier for drug products. In the United States, the FDA publishes the listed NDC numbers and the information submitted as part of the listing information in the NDC directory. The NDC directory is frequently updated. The drug products listed in the drug library 108, retrieved from the FDA, each include a unique NDC identifier. In an embodiment of the server 104, drug products are grouped together and considered interchangeable products of the same medication. This can be determined based on the FDA's definition of pharmaceutical equivalents.

Pharmaceutical equivalents are drug products in identical dosage forms and routes of administration that include identical amounts of the identical active drug ingredient. Pharmaceutical equivalents are the same medication. Pharmaceutical equivalents do not necessarily contain the same inactive ingredients and meet the identical compendial or other applicable standard of identity, strength, quality, and purity.

In addition to drug products, the drug library 108 may additionally include information on dietary supplements, vitamins, minerals, custom product entries, supplies, and other orderable products associated with the pharmaceutical supply chain.

In an embodiment, the pharmaceutical procurement server 104 communicates with the Wolters Kluwer's Medi-Span drug information database. The Medi-Span drug information database is a third-party solution that provides an easy to maintain and updated drug database. Some data fields included in the Medi-Span drug database include, for example, NDC, manufacturer, brand name, therapeutic equivalence code, package size, package type, medication description, drug enforcement agency schedule, storage condition, unit dose, and generic product identifier (GPI). These data points may be integrated into the pharmaceutical procurement server 104.

In an embodiment, because the pharmaceutical procurement server 104 is in communication with the drug library 108, users do not need to create medication profiles from scratch with the inherent risk of making errors in the medication profile. Instead, users can activate medication drug product groupings of pharmaceutical equivalents as identified in the drug library 108. As discussed herein, a "medication" may refer to a grouping of similar or functionally identical drug products. A single medication may be associated with multiple drug products, including drug products from different manufacturers, generic equivalents to brand names drug products, different delivery methods, different packaging methods, and so forth. These relationships between a medication and the multiple drug products rolling up to the medication can be defined based on the drug library's 108 grouping method and additional custom parameters for the pharmaceutical procurement server 104. These additional parameters can be provided upon request by a health system client. In an embodiment, the data operations for the pharmaceutical procurement platform 102 include custom grouping and organization of the information in the drug library 108.

In an embodiment, the grouping process includes identifying products that are in grams such as creams and ointments and grouping those products together with similar sized products. The grouping process may additionally include identifying products that are measured volumetrically and grouping those products together with equivalent products of comparable size.

In an embodiment, a user can implement medication specific overrides that allow health systems to have unique logic and requirements for each medication. A health system may indicate a supplier preference for a certain medication and/or a drug product preference for a certain medication. As discussed herein, a "drug product" may refer to a unique product and may identify the manufacturer, delivery method, packaging method, supplier, and so forth for that unique product. The pharmaceutical procurement server 104 may store an indication that a medication has a unique supplier preference order from the global supplier preference order. Additionally, the pharmaceutical procurement server 104 may store an indication that an ordering location prefers a certain drug product when fulfilling a medication need. Depending on the suppliers and their integration points, the pharmaceutical procurement server 104 redefines the sort of medications based on availability and other pre-identified factors such as cost, contracts, and so forth.

A user may implement drug product preferences based at least on supplier integration points, user-defined parameters, and government pricing program compliance. The logic executed by the pharmaceutical procurement server 104 redefines the preferred drug product sort when enabled. However, when disabled, the drug product preferences may be manually set by a user to ensure the health system defined preferred drug product will be presented to drug product buyers at each purchase.

In an embodiment, a user may implement location specific overrides. Location preferences may be made accessible only to administrators and those who are closely monitoring the pharmaceutical procurement server 104 reports and analytics. Because some locations have unique needs and patient populations, there are occasions for a location to operate outside of the general health system direction on a regular basis. Examples of various location specific needs include package size limitations, unit dosed or bulk-packaged, preferred drug product, preferred supplier, account type, and so forth.

The active directory 110 may be the directory of a health system or one or more healthcare entities. The active directory 110 may be a database comprising information relating to the health system, such as identifying information and contact information for practitioners, drug buyers, or employees associated with the health system. In an embodiment, the active directory 110 includes active directory federation services. In an embodiment, the active directory 110 includes information pertaining to the health system's employees such as their given name, last name, contact information, and so forth. The active directory 110 may be managed by the health system itself and only accessed by the pharmaceutical procurement server 104 via active directory federation services.

In an embodiment, the pharmaceutical procurement server 104 interfaces with a health system's active directory 110 by way of the active directory federation service (ADFS) by linking a username to a set of claims or attributes and validating those with the ADFS. As long as the email and user-entered password match the active directory 110, the claims will dictate the user profile they are linked to within the pharmaceutical procurement server 104.

The third-party administrator 112 is an outside party that provides information on regulations and/or ensures compliance with internal or government regulations. The third-party administrator 112 may be a software program that facilitates purchasing drug products compliantly under an applicable government drug purchasing program, such as a program that provides advantageous drug pricing under certain conditions. An example of such a drug pricing program is the 340B pricing program used in the United States. In operation, the third-party administrator 112 allows replenishing a pharmaceutical inventory with purchases made under specific drug purchase accounts based on retrospective evaluation of medication dispense and/or administration utilization records.

In an embodiment, the pharmaceutical procurement server 104 communicates with the third-party administrator 112 by way of an application program interface (API). The API integration allows the pharmaceutical procurement server 104 to ping the current medications being reviewed by a user of the pharmaceutical procurement platform 102 to indicate accumulations for the medication(s) and location(s) involved. This ping is generated by sending a TPA identifier(s) for the location(s) and the medication(s). The response ping carries the same data as the querying ping as well as the accumulations for specific account types. The accumulation data is displayed at the point of purchase as well as in other areas of the pharmaceutical procurement platform 102.

In an embodiment, the pharmaceutical procurement server 104 integrates via secure file transfer protocol (SFTP) and the third-party administrator 112 delivers flat files at a predetermined cadence. This kind of integration has the third-party administrator 112 delivering a static file with TPA identifiers, medication identifiers, and accumulations for specific account types. These can be delivered at an agreed upon cadence to an SFTP folder. The accumulation data is displayed at the point of purchase as well as in other areas of the pharmaceutical procurement platform 102.

The inventory management solution 114 can be an outside entity or system for inventory management. In an embodiment, the pharmaceutical procurement server 104 integrates with the inventory management solution 114 by way of SFTP and the inventory management solution 114 delivers flat files at a predetermined cadence. This type of integration has the inventory management solution 114 delivering a flat file with one or more of the following details for inventory visibility, including: device identification, device type, facility name, facility identification, item identification, current inventory, minimum and maximum inventory parameters, expiration data, inventory adjustment types and details, and so forth. The pharmaceutical procurement server 104 may use the inventory feed to allow users or machine learning algorithms to generate an order to replenish inventory. The pharmaceutical procurement server 104 may send information to the inventory management solution 114 by way of the SFTP to facilitate restocking at an inventory device. Inventory information is at the point of purchase, as well as in other areas of the pharmaceutical procurement platform 102.

In an embodiment, the inventory management solution 114 manages multiple locations and stock areas within an ordering location or health system. Some inventory locations utilize hardware and software to support the movement and storage of drug products. This creates perpetual inventory locations. The pharmaceutical procurement server 104 interfaces with the hardware and/or software vendors via EDI, API, event monitors, and other means to access key information from the perpetual inventory locations. Information received may include location identifiers, drug product identifiers, current inventory quantity, maximum inventory quantity, minimum inventory quantity, average usage, stock out event, lot, and expiration date. Additionally, the pharmaceutical procurement server 104 can send information to the hardware and/or software vendors to facilitate restocking inventory at the perpetual inventory device. Using this information, the pharmaceutical procurement server 104 can generate recommended orders, initial recommended orders, purchase orders, and show system-wide inventory availability and usage. In an embodiment, the pharmaceutical procurement server 104 has its own electronic perpetual inventory solution that can work with or independently of third-party perpetual inventory solutions and can interface with hardware vendors.

In an embodiment, the pharmaceutical procurement server 104 integrates with the inventory management solution 114 via SFTP and via electronic data interchange (EDI) files strictly for device replenishment. In such an embodiment, the inventory management solution 114 sends an EDI file with one or more of the following details, including: purchase order number, facility or location identifier, device identifier, item identifier, and quantity. The pharmaceutical procurement server 104 may ingest the EDI file and generate a shopping cart within the pharmaceutical procurement platform 102 with the necessary items. The pharmaceutical procurement server 104 sends an EDI file to the inventory management solution 114 indicating any changes to the original EDI file to prepare the device for replenishment.

The enterprise resource planning 116 may be an internal or external entity for resource planning. Enterprise resource planning 116 is a business process management software that allows an organization to use a system of integrated applications to manage the business and automate many back office functions related to technology, services, and human resources. The pharmaceutical procurement server 104 may communicate with enterprise resource planning 116 to exchange data pertinent to tracking pharmaceutical orders and payment of invoices, including sending order information so the enterprise resource planning 116 can generate a purchase order and then send receipt information for the purchase order.

In an embodiment, the server 104 manages and predicts drug shortages internally based on a variety of data within the system. In an embodiment, this is performed by a neural network that is trained on data for certain medications, classes of medications, or drug products within a healthcare location, health system, geographic region, and so forth. The data used to train the neural network may include drug pricing trends, purchasing and usage trends, backorder frequencies, common active pharmaceutical ingredients across existing shortages, past shortages, and shortage history of specific manufacturers. Each element is utilized in the neural network to deliver a shortage risk score for every medication. In the embodiment, the neural network analyzes these various data elements to deliver a shortage risk score for every medication, class of medications, or drug product. The neural network determines where there is likely to be an internal shortage of a certain medication, class of medications, or drug product at the ordering location(s).

In an embodiment, the pharmaceutical procurement server 104 integrates with the enterprise resource planning 116 by way of SFTP and may communicate by way of EDI files. In an embodiment, the pharmaceutical procurement server 104 sends the enterprise resource planning 116 carbon copies of EDI files along with receipt data. The enterprise resource planning 116 manages payments to external suppliers and the transfer of the general ledger (GL) without the manual export of a general ledger from the pharmaceutical procurement server 104. The general ledger is an accounting record. In the embodiments discussed herein, the general ledger may include a complete listing of all internal pharmaceutical sales and transfers. The general ledger may further include information one or more of: purchase order identifiers, ordering location identifiers, shipping location identifiers, medication descriptions, medication identifiers such as an NDC, quantity, unit price, total price, shipped date, received date, and so forth.

In an embodiment, the pharmaceutical procurement server 104 provides a general ledger export for a manual export and upload to the enterprise resource planning 116. In an embodiment, the pharmaceutical procurement server 104 is integrated such that the general ledger can be automatically exported or automatically reviewable and attainable. In an embodiment where automation is not attainable via integration, the general ledger can be manually exported by a user. The user can download and then manually upload or otherwise deliver to an enterprise resource planning.

The supplier 118 is an outside entity in communication with the pharmaceutical procurement server 104 by way of the network 120 connection. The supplier 118 may include any of a pharmaceutical manufacturer, a pharmaceutical wholesaler, a pharmaceutical distributor, an internal pharmaceutical procurement source, an external pharmaceutical procurement source, and so forth. In an embodiment, the pharmaceutical procurement server 104 communicates with the supplier 118 by way of an electronic data interchange (EDI). The electronic data interchange uses a secure file transfer protocol (SFTP) folder for delivery and pickup. In an embodiment, the pharmaceutical procurement server 104 provides the drug product buyer with ordering information regarding how, where, and what account to place an order on for those suppliers 118 unable to electronically integrate.

In an embodiment, suppliers 118 in communication with the pharmaceutical procurement server 104 are each assigned a unique supplier identifier based on the supplier type. Suppliers 118 represent unique ordering relationships for each health system using the pharmaceutical procurement server 104. The pharmaceutical procurement server 104 may store supplier information in connection with supplier 118 and that supplier's 118 relationship with a certain health system and their various accounts with the supplier 118, such as a healthcare facility's/location's account number and account type with the supplier 118. The pharmaceutical procurement server 104 establishes an EDI connection between suppliers 118 and each health system. Additionally, the pharmaceutical procurement server 104 may store supplier information in connection with certain ordering locations falling under the umbrella of the health system. In some implementations, the health system may have supplier 118 preferences that apply to all ordering locations within the health system, and in other implementations, the individual ordering locations within the health system may have their own supplier 118 preferences.

In an embodiment, the pharmaceutical procurement server 104 exchanges pertinent order data with suppliers 118. Order data may include, for example, a price file that is generated daily by the supplier 118 and sent via flat file or electronic data interchange. The prices may then be parsed and loaded into the pharmaceutical procurement server 104 to be displayed to a user by way of the user interface for the pharmaceutical procurement platform 102. Orders generated by the pharmaceutical procurement server 104 are parsed and formatted per electronic data interchange requirements. Orders are acknowledged by the supplier 118 by way of the electronic data interchange communication. This step may be represented in the user interface by transitioning the order status from pending to submitted and may include acknowledgement information received from the supplier 118.

In an embodiment, the pharmaceutical procurement server 104 communicates with the supplier 118 by way of an API. API integration with a supplier 118 can be implemented such that the pharmaceutical procurement server 104 has access to information about the supplier's 118 current, on-hand inventory. Additionally, through an electronic data interchange integration, the pharmaceutical procurement server 104 may have access to the supplier's 118 current pricing.

The pharmaceutical procurement server 104 is configured to select a supplier 118 out of one or more possible suppliers 118 for a certain medication, and then indicate to a user of the pharmaceutical procurement platform 102 which supplier is the most advantageous for purchasing the certain medication. Medications and drug products can come from multiple suppliers. Each supplier 118 can have a different drug product selection with some drug products overlapping with other suppliers. Suppliers usually have their own unique portal which displays key information in different ways. Some supplier portals have an online ordering portal, others require an email, fax, or phone call to place an order. Traditionally, it is difficult to know when to order from which supplier 118 and navigate each supplier with unique account information and credentials. Additionally, health systems may have an internal supplier 118 with drug products that they would prefer to utilize prior to purchasing drug products from an external supplier 118. The pharmaceutical procurement server 104 selects the correct supplier 118 for medications and drug products based on a plurality of factors. The pharmaceutical procurement server 104 can create and support the electronic infrastructure required for utilizing an internal supplier or supply information regarding an external supplier's order placement method. The pharmaceutical procurement server 104 incorporates electronic ordering connections with external suppliers 118 to send and receive some or all of the following information, including drug product catalogue with pricing, ordering files such as purchase orders, order acknowledgements, shipment notifications, invoices, and so forth, and real-time inventory quantities that could incorporate multiple supplier warehouses. The pharmaceutical procurement server 104 allows users to manually update supplier 118 drug products, identifiers, and catalogue prices when electronic integration is not available. When electronic integration is not available, the pharmaceutical procurement server 104 also allows users to manually enter order acknowledgement, tracking, and receipt data.

Additionally, the pharmaceutical procurement server 104 is configured to select an account with a supplier 118. In traditional systems, each healthcare ordering location may have multiple accounts with a single supplier 118. It is difficult to know which account should be used when ordering a certain medication. The accounts generally have different pricing and could be selected for a variety of reasons, such as based on government pricing system regulations, government compliance requirements, incorporating a third-party packaging solution to unit dose bulk drug products or individually label and barcode drug products, supplying different contract discounts, accessing a different supplier warehouse, and so forth. The pharmaceutical procurement server 104 selects the correct accounts for each ordered drug product by incorporating information from third-party administrators 112 and the supplier's 118 account-specific information.

The pharmaceutical procurement server 104 is additionally configured to select a quantity for each drug product ordered by a healthcare location. Each drug product ordered will turn at a different speed for each ordering location and at different stock areas within the ordering location. Therefore, it is important to know the quantity that should be ordered for each medication. In traditional systems, knowing what quantity to order relies greatly on an ordering user's experience with the ordering location and understanding of general ordering principles. Ordering too much leads to expired drug products and ordering too little leads to stock out events with corresponding adverse events to the health system's patients. Additionally, most suppliers' 118 package sizes differ from how a healthcare system uses a drug product and unit of measure conversion errors can lead to incorrect order quantities.

The pharmaceutical procurement server 104 is configured to calculate order quantities for different medications based on the health system's need and usage. The pharmaceutical procurement server 104 generates correct order quantities or makes recommendations to the ordering user.

In an embodiment, the pharmaceutical procurement server 104 allows users to order at the standard usable unit of measure, e.g., one table, one vial, etc. and automatically converts to the supplier's 118 package size, e.g. 1000 tables, 10 vials, etc. The pharmaceutical procurement server 104 can analyze some or all of the following information and present assessments to determine ideal ordering quantities, based on: historic purchasing, historic usage, historic expired inventory, risk of running out, risk of expiring, initial purchase price and holding cost, forecasted cost savings, forecasted shortage scenarios, perpetual inventory storage location configurations, physical storage space, and so forth.

In an embodiment as illustrated in FIG. 1, the pharmaceutical procurement server 104 is independent of one or more other server groups 112, 114, 116, 118. In an embodiment, the pharmaceutical procurement server 104 and one or more other server groups 112, 114, 116, 118 are not independent of one another. In such an embodiment, a single server group may include all information necessary for running the pharmaceutical procurement server 104, including user profile information, payment information, transaction history, drug product database information, pricing information, market inventory information, and/or information specific to one or more health systems or healthcare entities. It should be appreciated that numerous different configurations may be used without departing from the scope of the disclosure.

In an example method, the pharmaceutical procurement server 104 provides a the pharmaceutical procurement platform 102 comprising an ordering portal for ordering drug products. The ordering portal of the pharmaceutical procurement platform 102 presents one or more selectable medication items. The pharmaceutical procurement server 104 receives input via the ordering portal indicating preferences or procedures for purchasing and storing pharmaceuticals. The pharmaceutical procurement server 104 processes the input utilizing decision criteria (may be referred to herein as "product preferences") to provide one or more of: an initial recommended medication order or business analytic feedback. The pharmaceutical procurement server 104 may process the input based at least in part on business analytics data associated with selectable medication items or decision criteria. The ordering portal may receive additional input such as an initial recommended medication order or an update to a recommended medication order. Responsive to receiving the additional input, the pharmaceutical procurement server 104 may submit a pharmaceutical order to a supplier for the items within the recommended medication order. In an embodiment, the pharmaceutical procurement server 104 analyzes the product preferences, the medication needs of the ordering location, and the available inventory of multiple suppliers to generate an initial recommended order for the ordering location. A user may view the initial recommended order within the ordering portal. The user may make amendments or changes to the initial recommended order before the order is processed and the drug products are purchased.

In an embodiment, the drug product preferences for the ordering location are implemented by the pharmaceutical procurement server 104. The drug product preferences include, for example, medication supplier contract terms, medication supplier data, medication formularies, medication availability, drug product contract terms, drug product supplier data, drug product availability, supplier availability, accumulation availability for replenishment, medication pricing options, contractual pricing options, government program pricing options, utilization, and/or individual medication packaging characteristics such as size, expiration, or lot number. The medication pricing options may include government program pricing options. In an embodiment implemented in the United States, for example, the government program pricing options may include 340B Drug Discount Program pricing options. The drug product preferences may include a health system regulation, a regulation specific to the ordering location, or health system guidelines for pharmaceutical procurement. The drug product preferences may include package-type preferences, package-type requirements or restrictions, an indication of whether unit-dose or bulk packaging is preferred for certain medications or drug products, and so forth. The drug product preferences may include an indication of whether a medication or drug product is available from an internal supplier rather than an external supplier. The drug product preferences may include drug product shortage predictions and analysis.

In an embodiment, the pharmaceutical procurement platform 102 provides recommended drug product orders based on supply chain information. A supply chain includes the processes and systems involved in the drug product production, procurement, inventory, distribution, return, and destruction of items such as pharmaceuticals. The pharmaceutical procurement server 104 may receive supply chain information from the supplier 118, the third-party administrator 112, the enterprise resource planning 116, or any other suitable party.

In an embodiment, the pharmaceutical procurement platform 102 provides recommended drug product orders based on business analytics data. Business analytics data may include, for example, historical data, current data, forecasted data associated with purchasing, utilization, inventory, availability, pricing options, and contractual terms, individual purchasing organizations, systems, markets, and industries. Business analytics data can be collected and utilized by the pharmaceutical procurement server 104 to facilitate optimized purchasing for a supply chain.

In an example use-case, an employee of a health system is assigned to be the drug product buyer for a healthcare entity such as a hospital or clinic (referred to as an "ordering location"). The drug product buyer needs to order a medication for the ordering location. In traditional systems, the drug product buyer would log into a vendor's software and would place an order. This traditional system is not optimal, effective, intuitive, or associated with a logical standardized process. The pharmaceutical procurement platform 102 described herein provides an efficient, optimal, intuitive, and logical computer-based solution to pharmaceutical procurement. In accordance with the disclosures herein, the drug product buyer accesses the pharmaceutical procurement platform 102 to place an order for one or more medications. The drug product buyer searches for a medication and selects from the listed matches from the search. The drug product buyer may add a quantity of a certain medication and order the medication through a shopping cart. Once the shopping cart is confirmed, the pharmaceutical procurement server 104 automatically identifies one or more individual drug products to include in the order based on decision criteria, business analytics data, and/or user edits to the order. The example logic executed by the pharmaceutical procurement server 104 may include sorting medications based on what is available from the supplier, contract preference rating, and unit price. The logic may include filtering medications based on whether drug products from the ordering list could be ordered alone, whether current inventory is available from the supplier, and package type requirements. The package type requirements may default to indicate that any package is accessible or may include certain packaging requirements or preferences. The logic may include sorting medications based on supplier preference, contract preference rating, package size, appropriate drug product, appropriate supplier, appropriate supplier account, and modified unit price. A supplier preference may indicate that an ordering location wishes to favor certain pharmaceutical suppliers. For example, the ordering location may wish to prioritize internal suppliers or internal storehouses of pharmaceuticals before purchasing drug products from external suppliers. For example, the ordering location may wish to prioritize certain suppliers based on contractual agreements, drug rebate agreements, and so forth. The supplier preference may be an indication of how the ordering location wishes to prioritize suppliers when selecting a drug product. In an embodiment, the supplier preference may be referenced for sorting drug products after the drug products have already been sorted and/or filtered based on cost.

In an embodiment, the modified unit price of a drug product is determined based on typical usage of a medication at a healthcare location. For example, the modified unit price can be calculated based on an indication that any quantity of a medication that would not be used within a threshold time period, e.g. 90 days, is excessive. For example, if a healthcare site averaged fifty of a certain medication every 90 days, then a package of 100 of the certain medication at a price of $0.01 per dose would receive a modified unit price of $0.02 per does. This keeps the medications with larger package sizes within the ordering group but ranks them appropriately. This requires having accurate usage values, or when there is not accurate usage information, assuming that anything beyond the order value is excessive.

Figure 2:
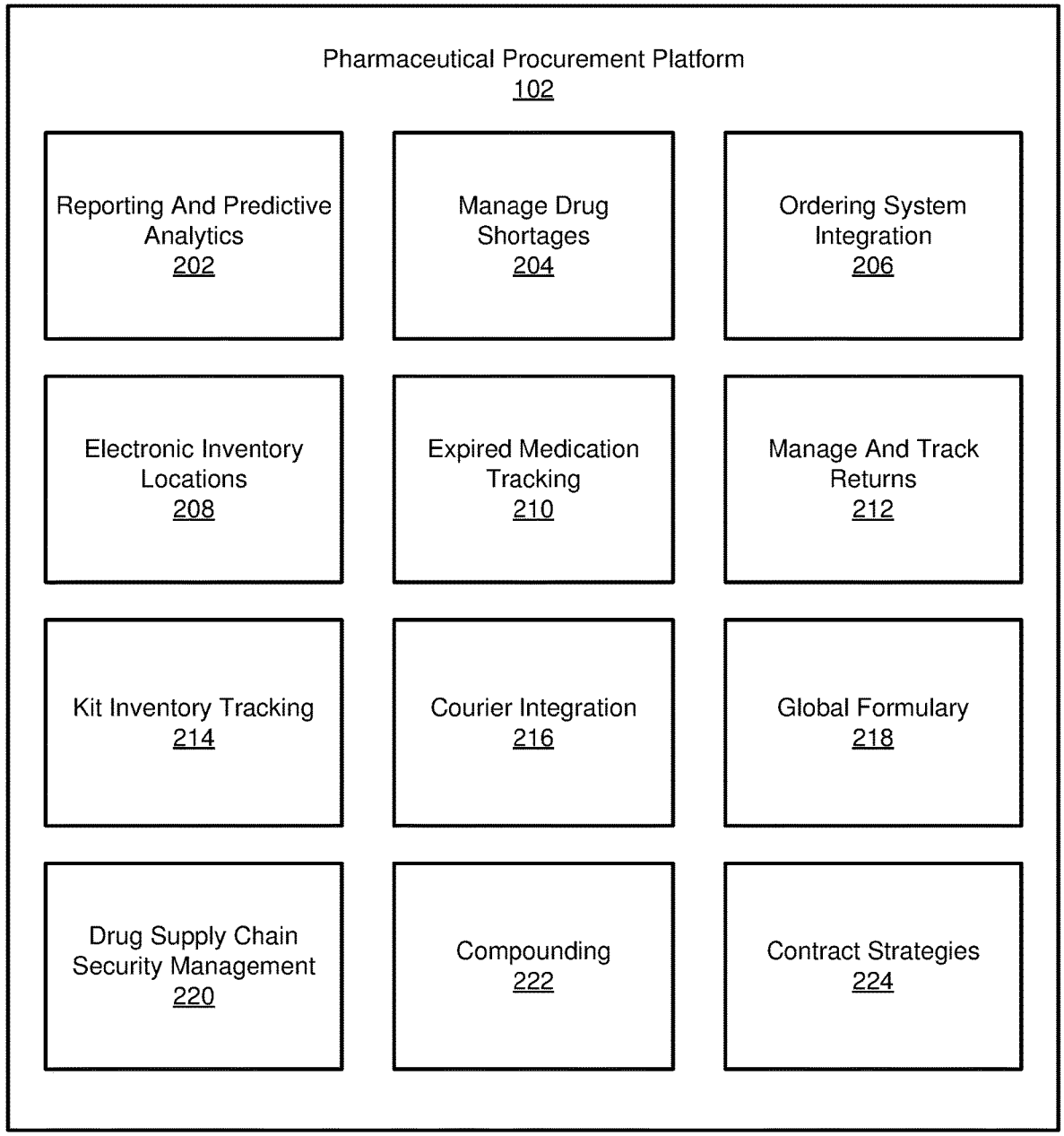
FIG. 2 is a schematic block diagram illustrating some components of a pharmaceutical procurement platform.

FIG. 2 is a schematic block diagram of one or more components and functionalities of the pharmaceutical procurement platform 102. The pharmaceutical procurement platform 102 is capable of running one or more processors capable of executing instructions stored in non-transitory computer readable storage medium to provide one or more of the functionalities illustrated in FIG. 2.

In traditional medicine purchasing systems, a drug product buyer must gain access to and then log into each supplier portal separately. The drug product buyer must track from which supplier to purchase each drug product, and which supplier requires email, phone call, fax, or web portal order placement. The drug product buyer must know all compliance factors for various suppliers, government agencies, and medications. The pharmaceutical procurement platform 102 alleviates these issues and provides a single ordering platform for all pharmaceutical orders.

A primary purpose of the pharmaceutical procurement platform 102 is to provide a simple user interface to a drug product buyer, and to facilitate pharmaceutical purchasing transactions based on predictions, analytics, and location-specific calculations. The pharmaceutical procurement server 104 generates an optimized shopping cart for health systems and individual healthcare locations based on the needs, trends, contracts, expenditures, and so forth for that entity. The pharmaceutical procurement server 104 generates the optimized shopping cart based in part on ordering logic. The ordering logic is the criteria used to determine which drug product, supplier, supplier account, and order quantity will be selected for each individual item being ordered. Ordering logic may include splitting a single line item order into multiple line items of different drug products, suppliers, supplier accounts, and quantities to maintain compliance and ensure the location is ordering sufficient quantities. Ordering logic may include holding a desired drug product order and placing the order when desired conditions are met. Ordering logic may be overridden if necessary and may include only certain aspects of the logic activated, based on the needs of the ordering location in combination with user-set preferences.

In an embodiment, the pharmaceutical procurement server 104 performs analytics to make drug product selection suggestions to a user. Most medications have multiple pharmaceutical equivalents available, frequently referred to as "generics." These equivalent medications are typically considered interchangeable for a healthcare system. The multitude of interchangeable options creates confusion as to which drug product should be ordered and creates inconsistency in drug product selection. The pharmaceutical procurement server 104 selects the correct drug product by removing the need for a drug buyer to make this decision. The pharmaceutical procurement server 104 incorporates a ranking and filter system for interchangeable drug products. The ranking and filter system considers criteria such as package size (e.g. 1000 tablet bottle versus 100 tablet bottle), package type (e.g. barcode on each individual item required for patient administration or unique storage requirement such as being placed in a robotic system), current inventory availability, historic inventory availability, consistency of inventory availability, accumulations, purchase price, and contract discounts and rebates with its usage requirements and class of trade restrictions.

The pharmaceutical procurement platform 102 provides functionality for reporting and predictive analytics 202 which may include drug product availability, drug product pricing, drug product needs, recommended drug products, contract compliance, contract load, weighted pricing, purchasing consistency/standardization opportunities, savings opportunities, contracting opportunities, and potential drug product shortages. In an embodiment, the reporting and predictive analytics 202 component performs data aggregation functions. Due to disparate systems and non-electronic processes, health systems cannot view pharmacy procurement data in a single location and the available data cannot be easily accessed and analyzed for trends and insights. The reporting and predictive analytics 202 component performs data aggregations for health systems such that the data can be analyzed.

The pharmaceutical procurement platform 102 is designed to function as a single ordering portal for all pharmaceutical purchasing for a health system or healthcare entity. Data across multiple healthcare locations within the health system is aggregated such that all of the data can be analyzed to identify trends.

In an embodiment, the reporting and predictive analytics 202 component performs pharmaceutical purchasing analytics. This may include tracking, trending, forecasting expenditures, forecasting volume, and pricing medications and drug products over time. These analytics can be done per-medication and/or per-drug product. In an embodiment, the analytics are parsed based on the supplier, the healthcare location, the facility, or health system-wide. This allows for the capture of health system policy compliance, government pricing program compliance, and contract optimization monitoring.

In an embodiment, the reporting and predictive analytics 202 component performs analysis on price changes and price forecasting which provides the health system with the ability to implement cost avoidance measures. This includes tracking price changes over time for certain medications, classes of medications, drug products, or types of medications for different treatment plans. These analytics can be done independently based on the supplier, manufacturer, client, project, healthcare location, and so forth.

In an embodiment, the reporting and predictive analytics 202 component performs price variance analytics which provides the health system with the ability to implement cost savings measures. This includes monitoring pricing loaded at a health system's primary wholesaler to identify potential price variances and the impact of those variances across accounts.

In an embodiment, the reporting and predictive analytics 202 component identifies opportunities for a health system to standardize medications and drug products across the health system which provides the health system with leverage in contract negotiations and the ability to maximize savings associated with a contract. This includes predicting savings opportunities and recommending certain medications.

In an embodiment, the reporting and predictive analytics 202 component monitors compliance to purchasing preferred drug products over time and by healthcare location. This includes tracking realized savings based upon compliance to those preferred drug products.

In an embodiment, the reporting and predictive analytics 202 component calculates weighted prices for the drug products. This includes calculating a weighted price for a given drug product based on the drug product's mix of wholesaler acquisition cost (WAC), government pricing program cost, and group purchasing organization (GPO) cost. These costs may be different for each account within the pharmaceutical procurement platform 102 and may therefore be different for each ordering location or health system. This enables a health system to identify the best priced drug product based upon that health system's mixture of medications and drug products.

In an embodiment, the reporting and predictive analytics 202 component performs high WAC analytics which helps health systems identify issues such as waste, missing administration documentation, and accumulation errors, and maximizes savings capture. This includes identifying drug products where the WAC percentage of drug products purchased is greater than a threshold. This includes calculating insights and reasons for the high WAC and how long the high WAC has been occurring.

In an embodiment, the reporting and predictive analytics 202 component performs inventory analysis. This includes providing users with the ability to view current inventory value, quantity, minimum, maximum, last cycle count, and earliest expiration for a specific drug product across devices, across the health system, or within a specific device. This allows a health system to capture expiring drug products and facilitate their distribution internally prior to the expiration date.

In an embodiment, the reporting and predictive analytics 202 component performs inventory transaction analysis. This includes tracking and trending inventory transactions over time to identify average daily usage, average quantity used when used, peak usage, and so forth.

In an embodiment, the reporting and predictive analytics 202 component monitors internal orders. This includes monitoring trends and provides access to details for all orders being placed within the same health system from one facility to another facility within the health system. This allows for the capture of health system policy compliance, government pricing program compliance, and identifies shortages and/or inadequate stock levels.

In an embodiment, the reporting and predictive analytics 202 component performs drug product and/or medication shortage analysis. In an embodiment, this includes determining a likelihood there is currently a shortage of a certain medication or drug product and predicting a likelihood that a medication or drug product will experience a shortage in the future.

The reporting and predictive analytics 202 may perform medication shortage analysis. This may include separate analysis for each of the drug products for a certain medication. Based on the separate analysis for each of the applicable drug products, the reporting and predictive analytics 202 can determine whether they may be a medication-wide shortage. Additionally, the reporting and predictive analytics 202 can make this determination for whether there may be a shortage for a certain delivery type of the medication, for example, for intravenous delivery of the medication, tablet delivery of the medication, oral suspension delivery of the medication, and so forth.

The reporting and predictive analytics 202 may perform drug product shortage analysis. This includes determining whether there is currently a shortage of a certain drug product or there is likely to be a future shortage of the drug product. This analysis may include identifying potential alternatives to the drug product when there is a shortage. For example, the analysis could include identifying that a different drug product with the same delivery method, e.g. intravenous, oral suspension, tablet, etc. but produced by a different manufacturer, is not experiencing a shortage.

The pharmaceutical procurement platform 102 provides functionality for managing drug product shortages 204. In traditional systems, it is extremely difficult to manage, track, and forecast medication shortages. Currently, shortage management is independently monitored and managed separate from the purchasing portal and there is no tool available for effective communication, management, and retention at the point of purchase. In an embodiment, the managing drug product shortages 204 component provides a simplified shortage management system with optimized communication tools. The component forecasts shortages and prompts automatic purchases for needed shortage items available at a supplier. Additionally, the component generates a backorder queue for internal suppliers. Additionally, the component can monitor inventory levels at external suppliers 118 and place orders automatically when inventory becomes available. Additionally, the component can monitor and consolidate allocations across the health system to optimize health system access to shortage medications.

In an embodiment, pharmaceutical procurement server 104 manages and predicts drug product shortages internally based on a variety of data within the system. In an embodiment, this is performed by a neural network that is trained on data for certain medications or classes of medications within a healthcare location, a health system, a geographic region, and so forth. The data used to train the neural network may include drug product pricing trends, purchasing and usage trends, backorder frequencies, common active pharmaceutical ingredients across existing shortages, past shortages, and shortage history of specific manufacturers. Each element is utilized in the neural network to deliver a shortage risk score for every medication. In an embodiment, the neural network analyzes these various data elements to deliver a shortage risk score for every medication and determines whether there is likely to be an internal shortage of a certain medication at the ordering location.

The pharmaceutical procurement platform 102 provides functionality for ordering system integration 206. The ordering system integration 206 may include integration with the Controlled Substance Ordering System (CSOS) in some embodiments. It should be appreciated that the ordering system integration 206 may include integration with any suitable ordering system. The pharmaceutical procurement platform 102 simplifies order placement and order fulfillment by combining all internal and external purchases and routes them to the appropriate supplier. For internal orders, ordering locations, medications, and quantities are clearly accounted for in a general ledger of journal entries that are automatically generated and easily exportable.

Internal suppliers have disparate systems for filling internal orders, placing orders of their own to other internal suppliers, and again for external suppliers. The ordering system integration 206 provides a single pharmaceutical procurement platform 102 for internal and external purchasing and internal order fulfilment. The ordering system integration 206 removes disparity between ordering systems and fulfilment systems and thereby reduces volatile compatibility. The pharmaceutical procurement server 104 serves as a single repository for all purchases, returns, expired medications, wasted drug products, and any other inventory movement. This data is available to the user via the pharmaceutical procurement platform 102.

The pharmaceutical procurement platform 102 provides functionality for managing electronic inventory locations 208 within a pharmacy or other pharmaceutical storage facility. There are a variety of inventory devices and software solutions within the components of health systems FIG. 3. Health systems do not have a single and/or a complete view of their inventory. The electronic inventory locations 208 component is a simplified perpetual inventory management interface with system-wide visibility. The electronic inventory locations 208 component can integrate via the network 120 and the inventory management solution 114 or standalone and provides a perpetual inventory solution that learns as part of a feedback loop which feeds other components of the platform 102. This optimizes inventory dollars. Additionally, components of the pharmaceutical procurement platform 102 and the electronic inventory locations 208 provides inventory management that is intuitive to pharmacy and non-pharmacy personnel and has advanced and basic presentation of data. In an embodiment, all pharmaceutical purchase and restock processes flow into a workflow which optimizes a user's time and effort and thereby simplifies frontline inventory management.

The pharmaceutical procurement platform 102 provides functionality for expired medication tracking 210. In traditional systems, users must manage various stages of expired medications across multiple software and non-software based solutions and then can attempt to aggregate the information. In an embodiment, the expired medication tracking 210 component offers simplified expired medication management that provides ease of internally supplying medications and diverting purchases to an internal supplier for medications approaching their expiration date. In an embodiment, the component provides an alert indicating the medications will expire soon. In an embodiment, the expired medication tracking 210 includes a neural network for optimizing inventory to further reduce expired medication waste. In an embodiment, this could include tracking the quantities expired, the value expired, generating inventory level suggestions, and reaccumulate for sites registered to participate in a government pricing program.

The pharmaceutical procurement platform 102 provides functionality for managing and tracking returns 212. The pharmaceutical procurement platform 102 provides functionality for managing and tracking returns 212 for both internal and external orders. In traditional systems, users typically must manually request return authorizations for returning individual drug product units. There are numerous issues inherent with this process, including errors, time delays, miscommunications, and so forth. In some instances, the workflow for returning a drug product unit is so complex that users will instead elect to return the drug product units without preauthorization. This can result in additional issues, including lost drug product, lost credits, misappropriated credits, and so forth. In an embodiment, the manage and track returns 212 functionality offers a simplified return authorization request process along with a streamlined return approval process. Requesting users are able to enjoy an optimized and transparent authorization request process for quick turnarounds on internal return authorizations. External returns, in traditional systems, require users to log back into the supplier 118 ordering portal to request a return authorization and then periodically check back into the portal for approval or denial. In an embodiment, the pharmaceutical procurement server 104 integrates with a supplier's SFTP 118a. The pharmaceutical procurement server 104 sends an EDI file to request a return authorization. The pharmaceutical procurement server 104 can ingest EDI files from the supplier's SFTP 118a and present the data received in a familiar format for the user within the pharmaceutical procurement platform 102.

The pharmaceutical procurement platform 102 provides functionality for kit inventory tracking 214. Kit inventory tracking 214 provides information on lists and quantities of drug products to be included in a drug kit. A drug kit may include a selection of drug products that might be used together in a certain course of treatment. The kit inventory tracking 214 may additionally include instructions for the drug kit and generate a printable label for the drug kit. The printable label may include the name of the drug kit along with a barcode to individually identify each drug kit. In an embodiment, an administrator may manage inputs into the drug kit lists and instructions. The administrator may create a label name for the drug kit.

In an embodiment, the kit inventory tracking 214 guides a user during the creation or restocking of a drug kit and permits the user to scan the drug products remaining within a used drug kit. The kit inventory tracking 214 generates a list of drug products and quantities needed to restock the drug kits. This may include decrementing the medication inventory used during the restock process from the current medication inventory location. This may additionally include incrementing the medication inventory of the finished drug kits. Because quantity of individual drug products within each drug kit and the number of kits are known, the kit inventory tracking 214 may additionally report the drug product inventory for each drug product throughout the location within the drug kits. During the restock process, the kit inventory tracking 214 module tracks the lot number and expiration date of each drug product within the drug kit and identifies the technician and pharmacist restocking and conducting the final check on the drug kit.

In an embodiment, the earliest expiration date for any drug product within the drug kit is assigned as the expiration date of the entire drug kit. As drug kits are removed from the inventory location within the ordering location to be restocked throughout the ordering location, the kit inventory tracking 214 module permits a user to indicate the final location of the drug kit within the ordering location. For example, if the ordering location is a hospital, then the user may indicate that the drug kit is located at a certain department, on a certain floor of the hospital, within a certain patient pod in the hospital, and so forth. This may be important for locating the drug kits throughout the ordering location as the drug products approach their expiration date or are recalled so that they can be removed from the drug kits and replaced. The Kit Inventory Module allows components of the health system to access the Kit lists and kit data is available for reporting and predictive analytics 202.

In an embodiment, the pharmaceutical procurement server 104 manages a pharmaceutical general ledger that includes journal entries for each internal transaction within the health system. The general ledger is exportable for the accounts payable department. In an embodiment, the pharmaceutical procurement server 104 manages a digital inventory solution that is valuable for health locations with an inventory management solution 114, those health locations that do not have an inventory management solution 114, and those that have a mixed inventory with some inventory loaded into an inventory management solution 114 and some inventory that is not. The digital inventory may be maintained in response to a user manually creating devices and adding stocked medications to digital shelves to track inventory. The digital shelves tracks minimum and maximum quantities for different medications, different package sizes, and different storage constraints, e.g., medications that need to be stored refrigerated, at room temperature, or frozen. The digital shelves tracks expiration data, cycle counts, and enables ease of reordering. In an embodiment, the pharmaceutical procurement server 104 imports data from an inventory management solution to enable inventory visibility within the pharmaceutical procurement platform 102. Importing data in this manner allows users to optimize inventory via the pharmaceutical procurement server 104 analytics and reporting tools 202. Importing data further facilitates a level of inventory visibility not found in traditional systems in the industry, as current IMS 114 typically only give visibility to a single location's inventory and does not integrate across a health system or aggregate their inventories.

The pharmaceutical procurement platform 102 provides functionality for courier integration 216. The pharmaceutical procurement server 104 works with various tracking tools to identify anticipated arrival time of drug products, display tracking status updates, and obtain proof of delivery information. In one embodiment, the server 104 interfaces with an external courier tracking tool via API to facilitate drug product movement tracking from an external or internal supplier to facilities within the healthcare system. In one embodiment, the pharmaceutical procurement server 104 interfaces with an internal courier tracking portal to display tracking information within the pharmaceutical procurement platform 102.

The pharmaceutical procurement platform 102 provides functionality for a global formulary 218. In traditional systems, industry standards for formulary management do not allow for management or restriction of various formulary needs pertaining to various ordering groups. The global formulary 218 has a broad formulary that serves as a source for client-defined sub-formularies.

A formulary is a list of medications that have been authorized for purchase, storage, and dispensing within a health system or at a certain ordering location within the health system. As discussed herein, a formulary or sub-formulary may be referred to as "medication ordering permissions" for an ordering location or health system. A formulary may identify restrictions and limits associated with certain medications or drug products. A formulary may provide guidance on which medications or drug products should be used for different treatment strategies and allow for interchanging one prescribed medication or drug product with another. A formulary may exist at the corporate level of a health system with additional formularies and restrictions and policies being in place at each ordering location within the health system. In traditional systems, the industry standard for formulary management does not allow for management or restriction of various formulary needs pertaining to healthcare facility classes of trade.

The global formulary 218 includes a broad formulary that serves as a source for client-defined sub-formularies. In an example implementation, a health system has activated 2000 medications as being approved for ordering, with a hospital having access to order all drugs products for those medication. The formulary may include clarifying restrictions on several of the 2000 medications. A clinic within the health system may have a sub-formulary that provides the clinic with access to only a portion of the 2000 medications that are approved for the health system. For example, an outpatient clinic may have permission to order only 50 of the 2000 approved medications while a hospital has permission to order all 2000 of the 2000 approved medications. The formularies and sub-formularies prevent users from ordering medications that they should not order and follows the designated pathways for restricted and designated non-formulary purchases.

In traditional systems, when dealing with multiple layers of a facility and/or health system, various purchasing groups warrant access only to particular medications. It is inappropriate, but the industry standard in traditional systems is to allow all purchasers access to the broadest drug product list possible. Sub-formularies in the pharmaceutical procurement server 104 solve this problem. As the formulary is created by activating medication within the pharmaceutical procurement platform 102, which utilizes the modified groupings created by the server 104 in association with the data import from the library 108, sub-formularies can be created by activating the medications already activated within the formulary. In other words, the formulary represents all medications allowed to be ordered at the highest level (typically the health system level) and sub-formularies represent controlled access for the various sub-level purchasing groups such as regions, hospitals, clinics, departments, and so forth.

In an embodiment, the pharmaceutical procurement server 104 receives an indication of medication ordering permissions for a health system, an ordering location, or an account. In an embodiment, an ordering location and/or health system includes unique accounts for multiple drug product buyers at the ordering location, and in such an embodiment, each of the unique accounts and/or ordering locations may have unique medication ordering permissions. In an embodiment, medication ordering permissions are defined for all ordering locations within a health system. In an embodiment, medication ordering permissions are defined for classes of ordering locations within the health system, for example, hospitals may have broad medication ordering permissions and clinics may have narrow medication ordering permissions. The medication ordering permissions provides a listing of medications and/or drug products that an ordering location is permitted to obtain or dispense to patients, or vice versa, the medication ordering permissions provide a listing of medications and/or drug products the ordering location is not permitted to obtain or dispense to patients.

The pharmaceutical procurement platform 102 provides functionality for drug supply chain security management 220. This is to address and comply with government drug supply chain security legislation. In an embodiment, drug supply chain security management 220 may integrate with suppliers 118 for receipt of electronic records pertaining to the drug supply chain via EDI and/or API. In an embodiment, the platform 102 allows users to manually enter drug supply chain security data. The platform 102 also allows for supply chain data retention, validation, and exportation.

The pharmaceutical procurement server 104 provides functionality for the management of drug shortages 204. In traditional systems, shortages are generally identified after an order has been zero filled by a supplier. The pharmaceutical procurement server 104 analyzes and assesses data to identify and predict potential drug shortages. The pharmaceutical procurement server 104 maintains historical records of shortage management and communications to allow for subsequent reference and utilization.

The pharmaceutical procurement platform 102 provides functionality for compounding 222. Compound drugs include two or more individual drug product components and may be created by licensed pharmacy personnel. The compounding 222 component includes recipes for compound drugs and outlines the individual drug product ingredients for creating the compound drug. The compounding 222 component additionally includes instructions for making the compound drug and generates printable labels for labeling the compound drug.

In an embodiment, an administrator may manage and input the recipes and instructions for compound drugs. Additionally, the administrator may include supporting information and literature to support the efficacy, safety, and stability of the compound drug. The compounding 222 component is integrated with the electronic inventory locations 208 for optimized workflow for decrements and increments. The wastage of original drug products, if any, is tracked by the compounding 222 and electronic inventory locations 208 components. Compounding 222 allows all components of the health system 302 to access the recipes and compounding data for reporting and predictive analytics 202.

The pharmaceutical procurement platform 102 provides functionality for managing and analyzing contract strategies 224. Strategies for contracting drug products can vary depending on a variety of factors. Example factors include the form or dispensing method of the medication, for example whether the drug product is for intravenous use, oral solid, oral suspension, injectable, topical, and so forth. Additionally, the factors may include the competitive status of the drug product, for example whether the drug product is the sole source for that medication, whether there are multiple branded drug products and sources for the medication, and whether the drug product is the generic form of the medication. The factors may additionally include the therapeutic class, benchmark data, distribution sources, price trends, health system utilization, and so forth.

In an embodiment, the pharmaceutical procurement server 104 classifies the drug products based on these factors and makes contract recommendations for specific drug product or medications to realize cost savings opportunities. In an example implementation, the contract strategies 224 component identifies opportunities to standardize to a single drug product across the entire health system. The contract strategies 224 component evaluates available drug products, drug products purchased, current prices, including prices mandated by government pricing programs or other contracts, and utilization mix to develop a weighted mix price and recommends a preferred drug product based upon these factors. The contract strategies 224 component estimates annual cost savings if the recommendation is implemented and will track realized savings once the recommendation is implemented.

FIG. 3 is a schematic block diagram of example components of a health system 302. A health system 302 may include hospitals 304, clinics 306, surgical centers 308, pharmacies 310, urgent care 312 facilities, practitioners 314, consolidated service centers 316, and others. Each of the components of the health system 302 may follow guidelines or protocols determined by the health system 302, may follow individual protocols, or may follow a combination of individual protocols and protocols determined by the health system 302. In some instances, the health system 302 orders pharmaceuticals for one or more of the entities falling under the umbrella of the health system 302. In some instances, one or more of the entities within the health system 302 are responsible for procuring their own pharmaceuticals.

Figure 4:
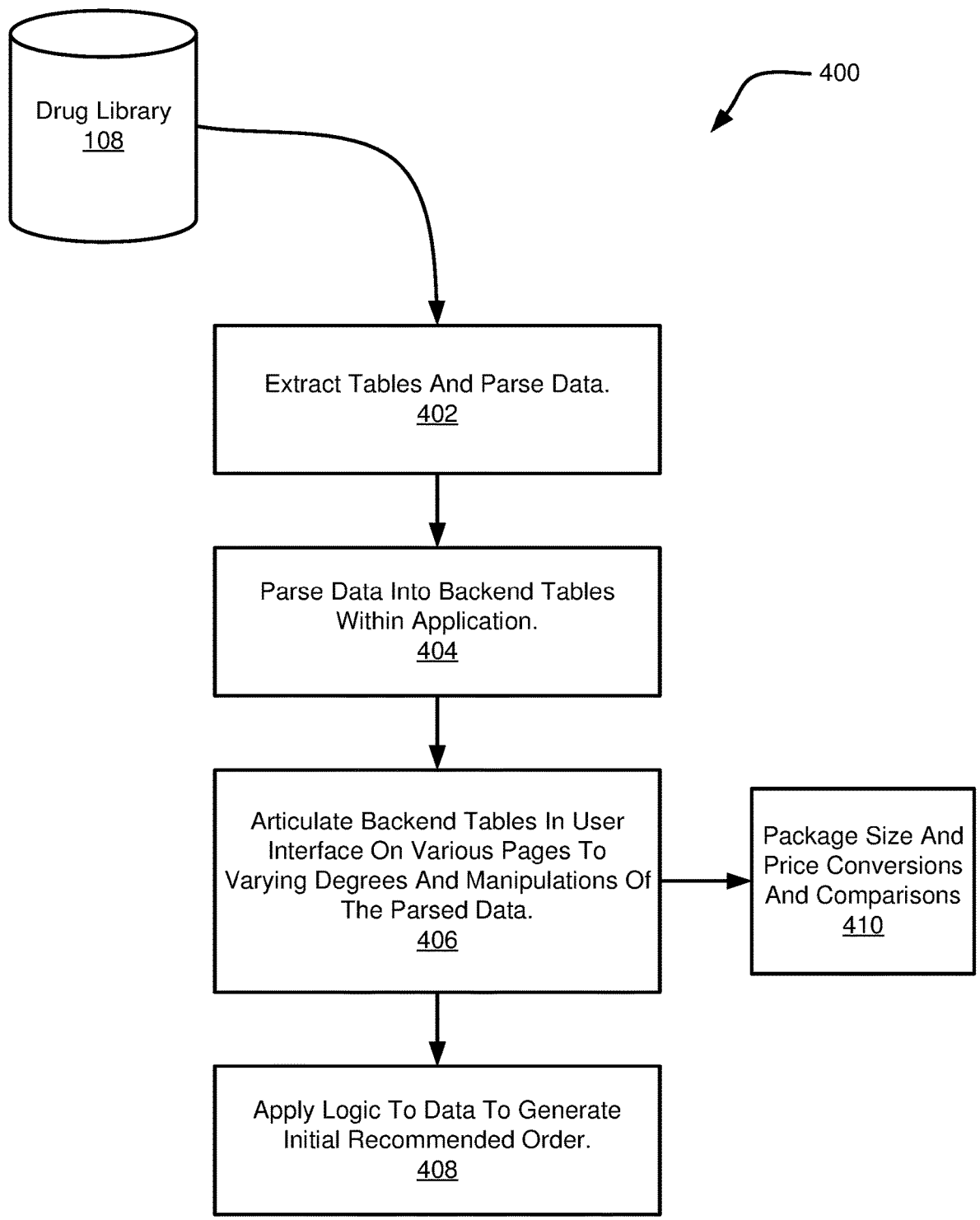
FIG. 4 is a schematic flow chart diagram of a process for communicating with a drug library and applying logic to information retrieved from the drug library.

FIG. 4 is a schematic diagram of a process 400 for communications between a drug library 108 and a pharmaceutical procurement server 104. The process 400 includes extracting tables from the drug library 108 and parsing that data (see 402). The process 400 includes parsing at 404 data into backend tables within the pharmaceutical procurement server 104. The process 400 includes articulating at 406 backend tables within a user interface for the pharmaceutical procurement platform 102 on various pages to varying degrees and manipulating the parsed data. Further to this, the process 400 includes performing conversions and comparisons at 410 on package size and price. The process 400 includes applying at 408 logic to the data retrieved from the drug library 108 to generate an initial recommended order.

Figure 5:
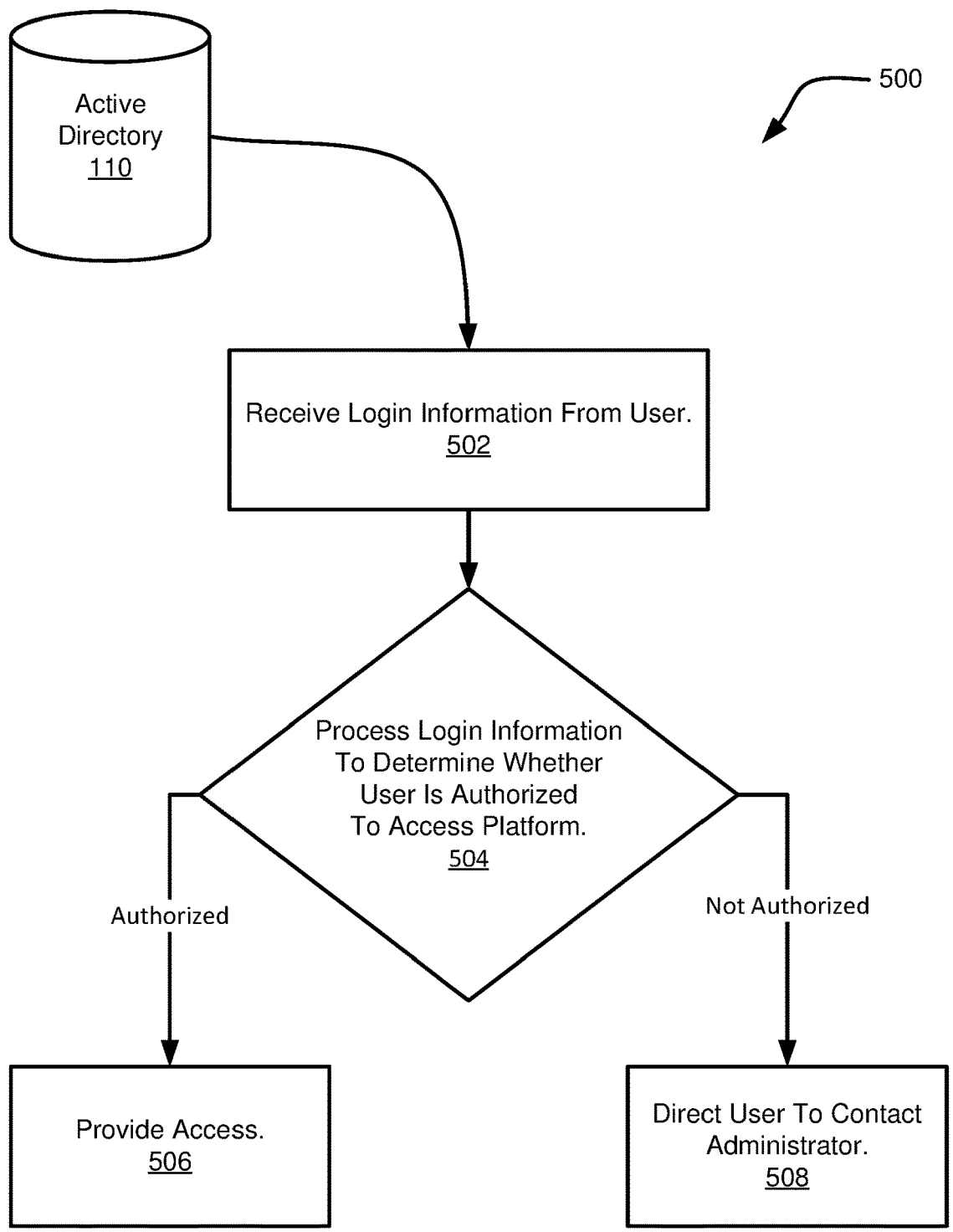
FIG. 5 is a schematic flow chart diagram of a process for communicating with an active directory and logging into an active directory.

FIG. 5 is a schematic diagram of a process 500 for communications between an active directory 110 and a pharmaceutical procurement server 104. The process 500 includes receiving login information at 502 from a user for logging into an active directory 110. The process 500 includes processing at 504 the login information to determine whether the user is authorized to access the platform 102. Upon determining the user is authorized to access the platform 102, the process 500 includes providing access to the user at 506. Upon determining the user is not authorized to access the platform 102, the process 500 includes directing the user to contact an administrator at 508.

Figure 6:
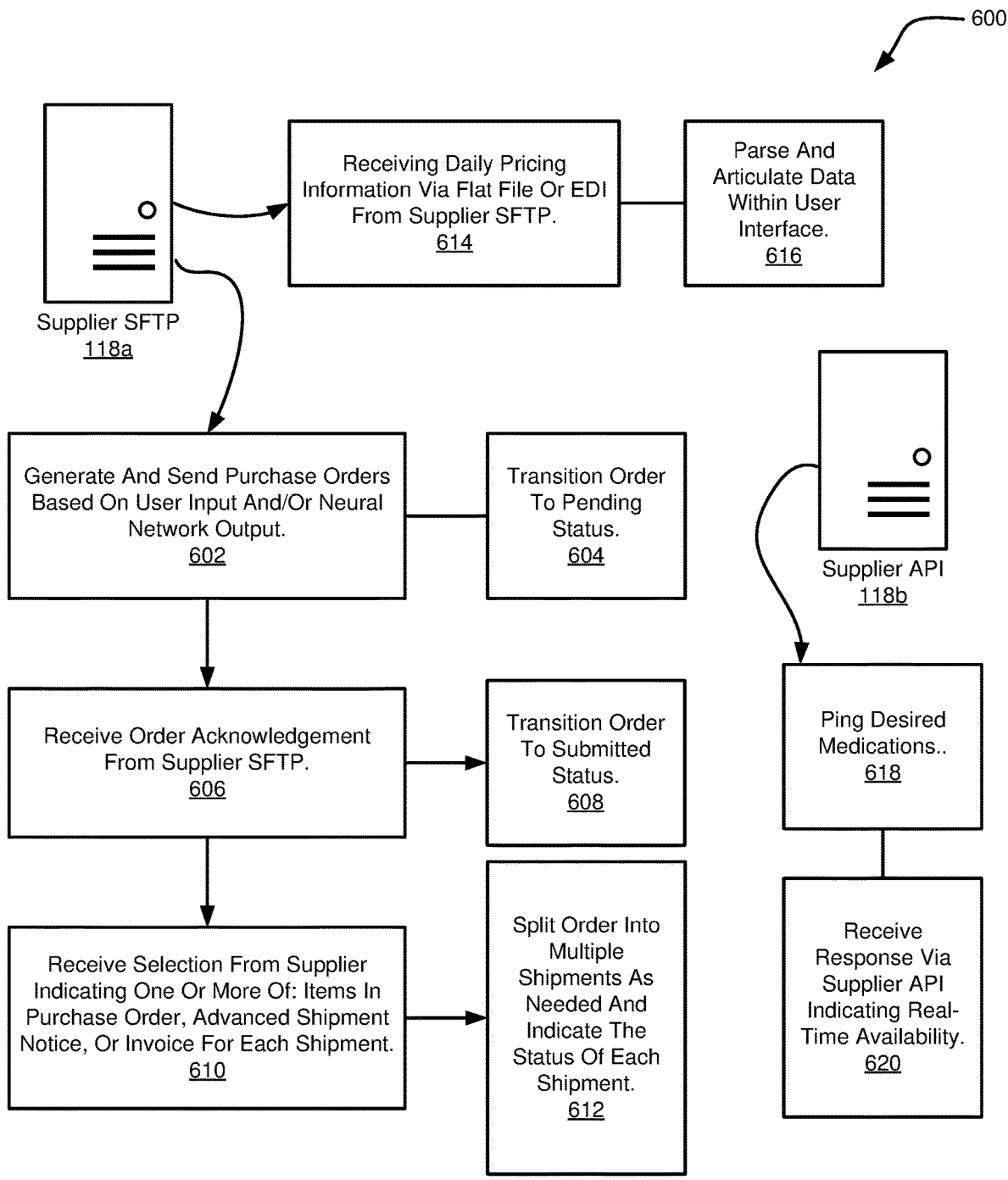
FIG. 6 is a schematic flow chart diagram of communication with a supplier and applying logic to the information retrieved from the supplier.

FIG. 6 is a schematic diagram of a process 600 for communications between a supplier secure file transfer protocol (SFTP) 118*a* and a pharmaceutical procurement server 104. The process 600 includes receiving information from the supplier SFTP 118*a* and generating and sending purchase orders based on user input and/or neural network output at 602. In an embodiment, the pharmaceutical procurement server 104 includes a neural network or is in communication with a neural network. The neural network is configured to analyze purchasing trends and usage trends for a healthcare ordering location and outputs suggested purchase orders and optimizations to purchasing decisions. The process 600 includes, in response to generating and sending the purchase orders at 602, transitioning at 604 the order to pending status within the pharmaceutical procurement platform 102. The process 600 includes receiving at 606 an order acknowledgement from the supplier SFTP 118*a*. Then, the process 600 includes transitioning at 608 the order to submitted status. The process 600 includes receiving at 610 a selection from the supplier indicating one or more of: items in the purchase order, advanced shipment notice, or an invoice for each shipment. Then, the process 600 includes splitting at 612 the order into multiple shipments as needed to indicate the status of each shipment. The process 600 includes receiving at 614 daily pricing information via flat file or EDI from the supplier SFTP 118*a*. The process 600 includes parsing and articulating the data at 616 within the user interface for the pharmaceutical procurement platform 102.

The process 600 further includes communicating with a supplier Application Program Interface (API) 118*b*. The process 600 includes pinging desired drug product at 618. The desired drug product may be communicated to the supplier API 118*b* by using an identifier for the drug product. The process 600 includes receiving at 620 a response via the supplier API 118*b* indicating real-time availability for the drug product.

Figure 7:
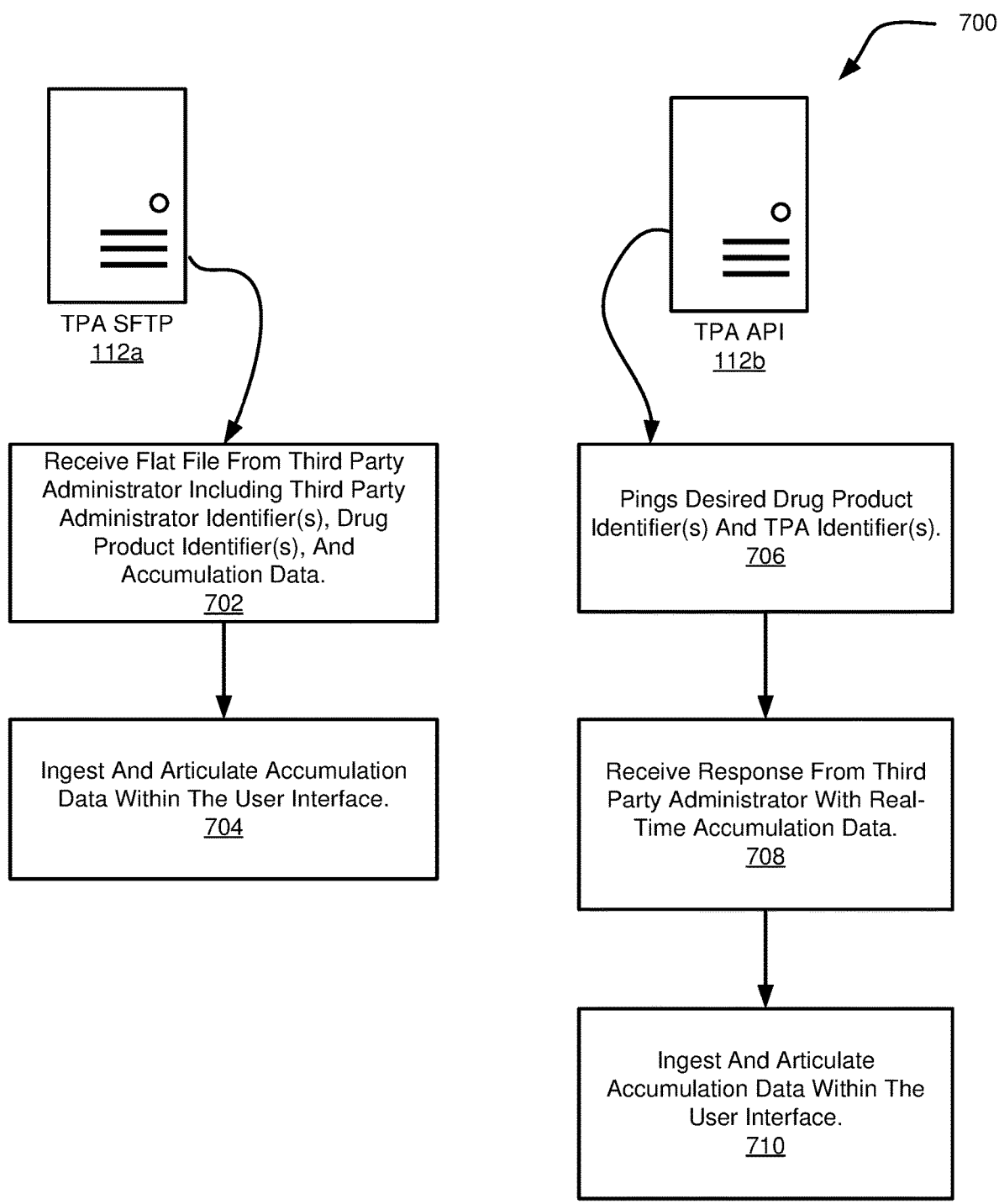
FIG. 7 is a schematic flow chart diagram of communications with a third-party administrator and applying logic to the information retrieved from the third-party administrator.

FIG. 7 is a schematic diagram of a process 700 for communications between a pharmaceutical procurement server 104 and a third-party administrator secure file transfer protocol (TPA SFTP) 112*a* and a third-party administrator application program interface (TPA API) 112*b*. In an embodiment, the pharmaceutical procurement server 104 receives at 702 from the third-party administrator SFTP 112*a* a flat file including TPA identifier(s) and, drug product identifier(s) (such as the NDC), and accumulation data. The pharmaceutical procurement server 104 ingests and articulates at 704 the accumulation data within the user interface of the pharmaceutical platform 102.

In an embodiment, the pharmaceutical procurement server 104 pings at 706 the third-party administrator API 112*b* with drug product identifier(s) and TPA identifier(s) with the intent of receiving accumulation information pertaining to the drug product identifier(s) and TPA identifier(s). The process 700 includes receiving at 708 responses from the third-party administrator with real-time accumulation data. The process 700 includes ingesting and articulating at 710 the accumulation data within the user interface of the pharmaceutical procurement platform 102.

Figure 8:
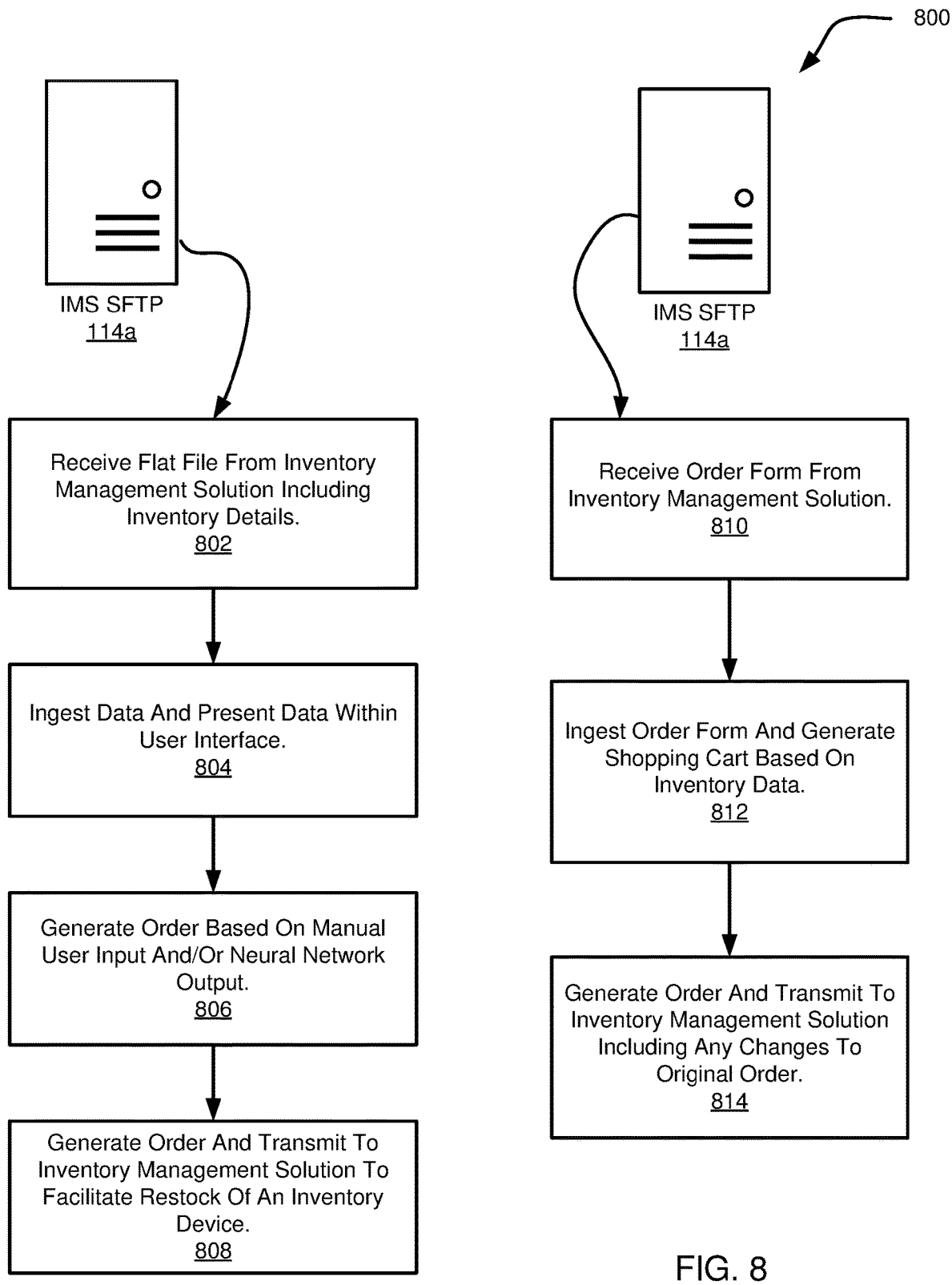
FIG. 8 is a schematic flow chart diagram of communications with an inventory management solution and applying logic to the information retrieved from the inventory management solution.

FIG. 8 is a schematic diagram of a process 800 for communications between a pharmaceutical procurement server 104 and an inventory management solution secure file transfer protocol (IMS SFTP) 114*a*. The process 800 includes the pharmaceutical procurement server 104 receiving at 802 a flat file from the inventory management solution 114 including inventory details. The pharmaceutical procurement server 104 ingests and presents the data at 804 within the user interface of the pharmaceutical procurement platform 102. The pharmaceutical procurement server 104 generates an order at 806 based on manual user input and/or neural network output. The process 800 includes generating and transmitting an order at 808 to the inventory management solution 114 to facilitate restock of an inventory device.

In an embodiment, the process 800 includes the pharmaceutical procurement server 104 receiving at 810 an order form from the inventory management solution SFTP 114*a*. The pharmaceutical procurement server 104 ingests the order form and generates a shopping cart at 812 based on the order form. The process 800 includes generating and transmitting an order at 814 to the inventory management solution 114 including any changes to the original order.

Figure 9:
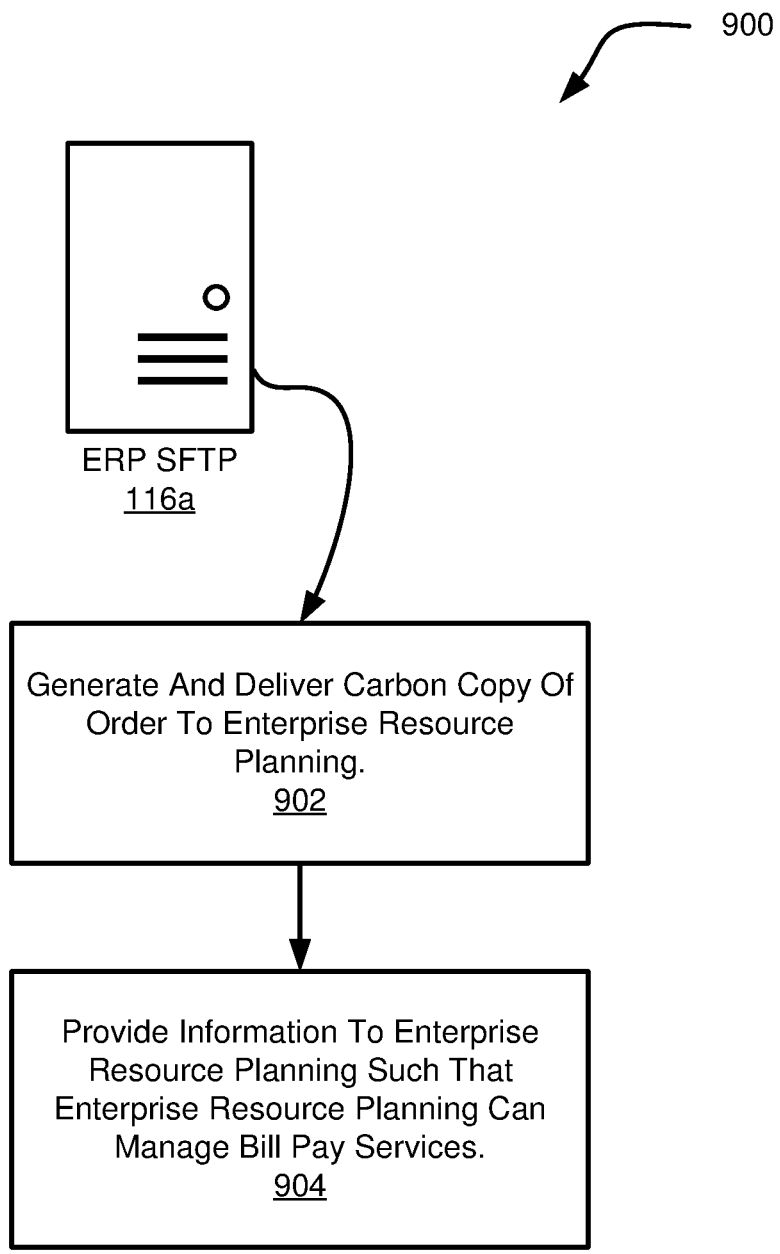
FIG. 9 is a schematic flow chart diagram of communications with an enterprise resource planning secure file transfer protocol (SFTP)

FIG. 9 is a schematic diagram of a process 900 for communications between a pharmaceutical procurement server 104 and an enterprise resource planning secure file transfer protocol (ERP SFTP) 116a. The process 900 includes the pharmaceutical procurement server 104 generating and delivering at 902 a carbon copy of an order to the enterprise resource planning 116. The process 900 includes providing information at 904 to the enterprise resource planning 116 such that the enterprise resource planning 116 can manage bill pay services.

Figure 10:
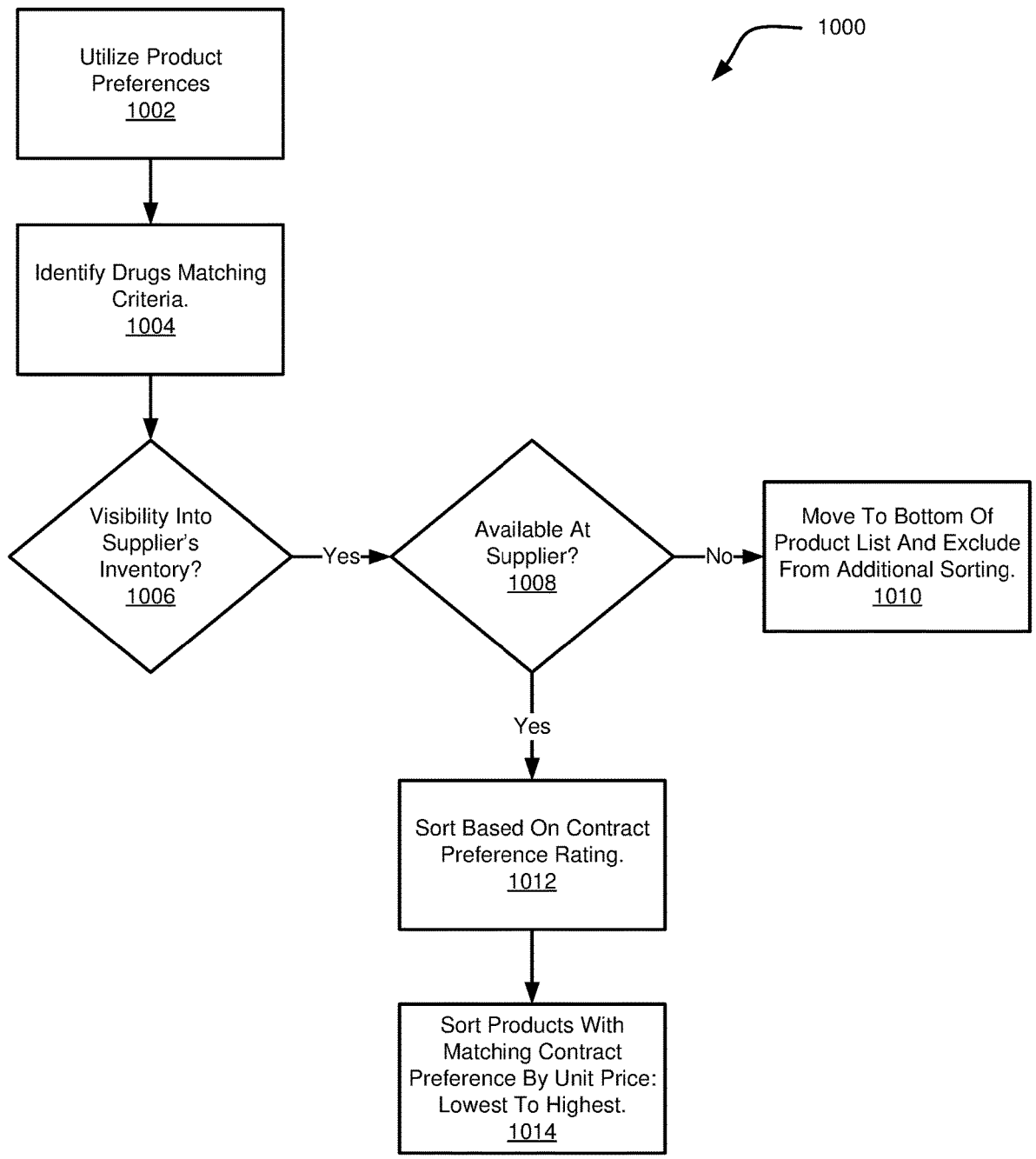
FIG. 10 is a schematic flow chart diagram of a process flow for identifying medications based on drug product preferences and sorting the identified medications.

FIG. 10 is a schematic diagram of a process 1000 for applying preferences set in the pharmaceutical procurement platform 102 to a shopping cart whereby to identify an initial recommended order. In an embodiment, the process 1000 is triggered by a user who has built a shopping cart manually or with a neural network and is now processing the order. The process 1000 includes the pharmaceutical procurement server 104 utilizing the 1002 drug product preferences. The drug product preferences may be manually input by a user, determined based on preferences, determined based on government program regulations, determined based on health system compliance regulations, determined based on contractual agreements, and so forth. The process 1000 includes identifying at 1004 drug products matching the criteria. The process 1000 includes gaining visibility at 1006 into the supplier's 118 inventory. This may be accomplished by way of an API communication with a supplier 118. If there is a means to communicate with the supplier 118 at 1006, the process 1000 includes determining whether the drug product is available at the supplier 118 at 1008. If the drug product is not available at the supplier 118 as determined at 1008, the process 1000 includes moving the drug product to the bottom of the drug product list and excluding the drug product from additional sorting at 1010. If the drug product is available at the supplier 118 as determined at 1008, the process 1000 includes sorting based on contract preference rating at 1012 and sorting drug products with matching contract preference by unit price: lowest to highest at 1014.

In an embodiment, a purchasable drug product is identified based on a plurality of decision criteria factors. The decision criteria factors can be applied, for example, to a medication drug product group. A medication drug product group is a list, such as a selectable drug product item list, of interchangeable drug products (pharmaceutical equivalents). These drug products may be identified based on data stored in the drug library 108. Decision criteria may include unit price, contracts with various suppliers, healthcare locations, health systems, manufacturers, and so forth, package types such as bulk, unit dosed, robot-ready, syringe, vial, and so forth, suppliers such as internal, wholesalers, or direct, availability including current and historical availability, government pricing, package size, government 340B drug discount program accumulation data, utilization data, and expiration data.

In an embodiment, the ordering logic for identifying drug products to be ordered includes the following. Product groups are sorted based on what drug products are available from a supplier. This may be done regardless of current inventory. Product groups are sorted based on contract preference rating, and this could be a globally set ranking. Products are sorted based on unit price from lowest to highest. Product groups are then filtered. The drug product groups may be filtered to favor internal suppliers over external suppliers. The drug product groups may be filtered to remove any drug products that do not have current inventory available from the supplier 118, if that information is known. The drug product groups may be filtered based on package type requirements. The drug product groups may then be sorted again. The drug product groups may be sorted based on supplier preference, contract preference rating, package size, and/or modified unit price. The top available drug product may be selected by picking the top item on the filtered/sorted drug product list.

In an embodiment, the pharmaceutical procurement server 104 addresses the quantity available for a drug product but finds it is insufficient to complete the requested order. In such an embodiment, the pharmaceutical procurement server 104 informs a user that a new drug product is being purchased. However, the user will be able to manually override and purchase the initial drug product from another supplier or otherwise change either the drug product or supplier selection, as desired. All manual overrides are included in the reporting and analytics 202 for compliance tracking.

In an embodiment, the pharmaceutical procurement server 104 generates recommended orders to restock an internal supplier found within the health system 302 which supplies drug products to ordering locations participating in a government pricing program. A review of location specific accumulations could be performed and used to generate orders on the accumulating location's bill to/ship to account to restock the internal supplier, to maintain compliance, and to optimize the health system's 302 participation in the government pricing program. Any purchases made with bill to/ship to accounts in this scenario will be tracked and maintained by the server 104 via an accounting process. If there are no accumulations available, the internal supplier will order on its own account(s).

In an embodiment, the pharmaceutical procurement server 104 executes 340B ordering logic for locations participating in a government pricing program when ordering from an internal supplier. The 340B ordering logic may be implemented to sort medications based on whether the drug products have accumulations or any reserves within the accounting process and may further be used to sort drug products based on unit price or weighted unit price. When a location orders from an internal supplier, the internal supplier ships the drug products, considering and adjusting the accounting process reserves as necessary. The server 104 will send an EDI feed to the TPA 112 to decrement the accumulations, when necessary, to maintain compliance with the government pricing program. Delivered drug products will be recorded in the general ledger and billed at the appropriate price.

Figure 11A:
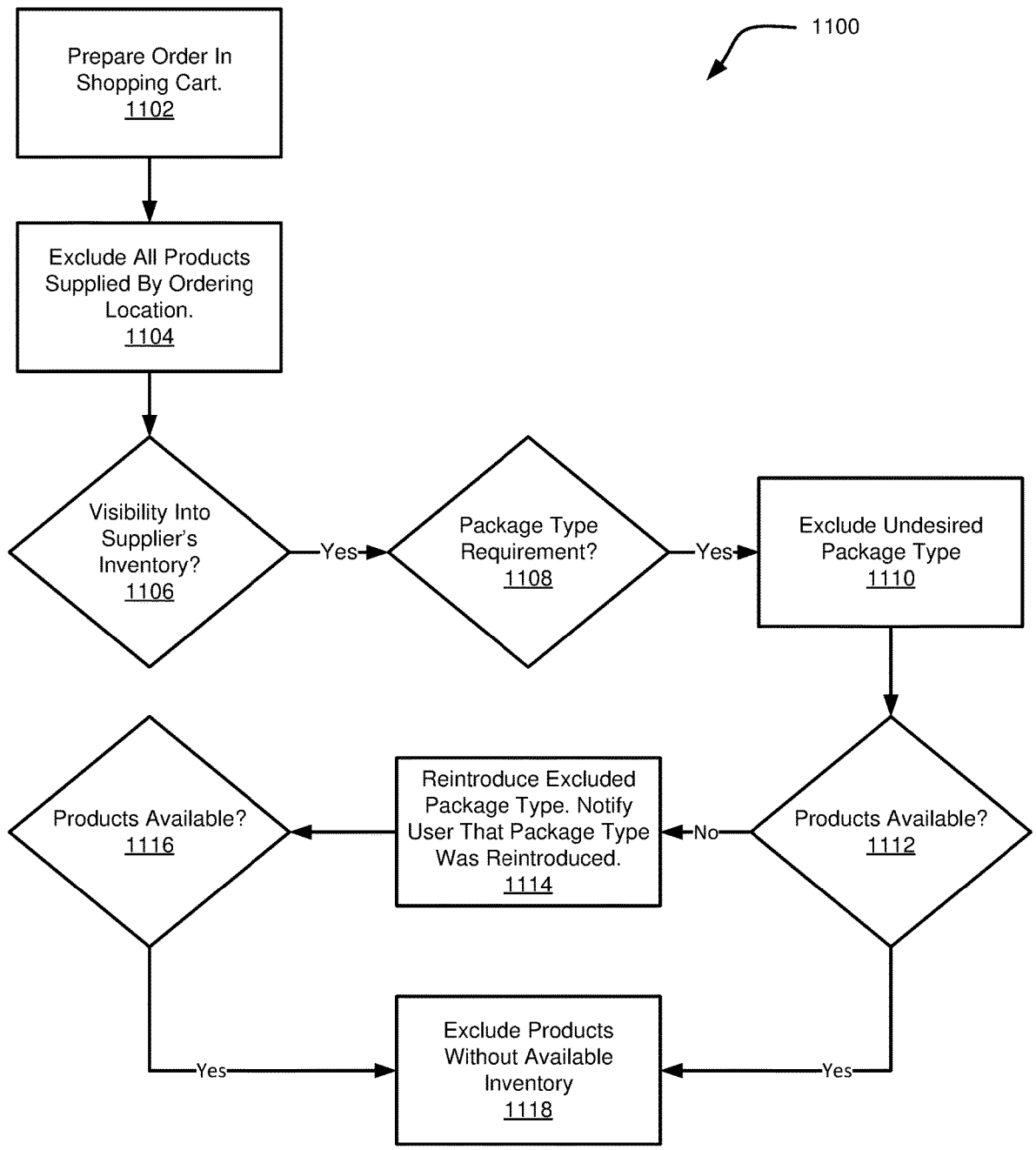
FIGS. 11A and 11B illustrate a schematic flow chart diagram of a process flow for identifying and sorting medications.
Figure 11B:
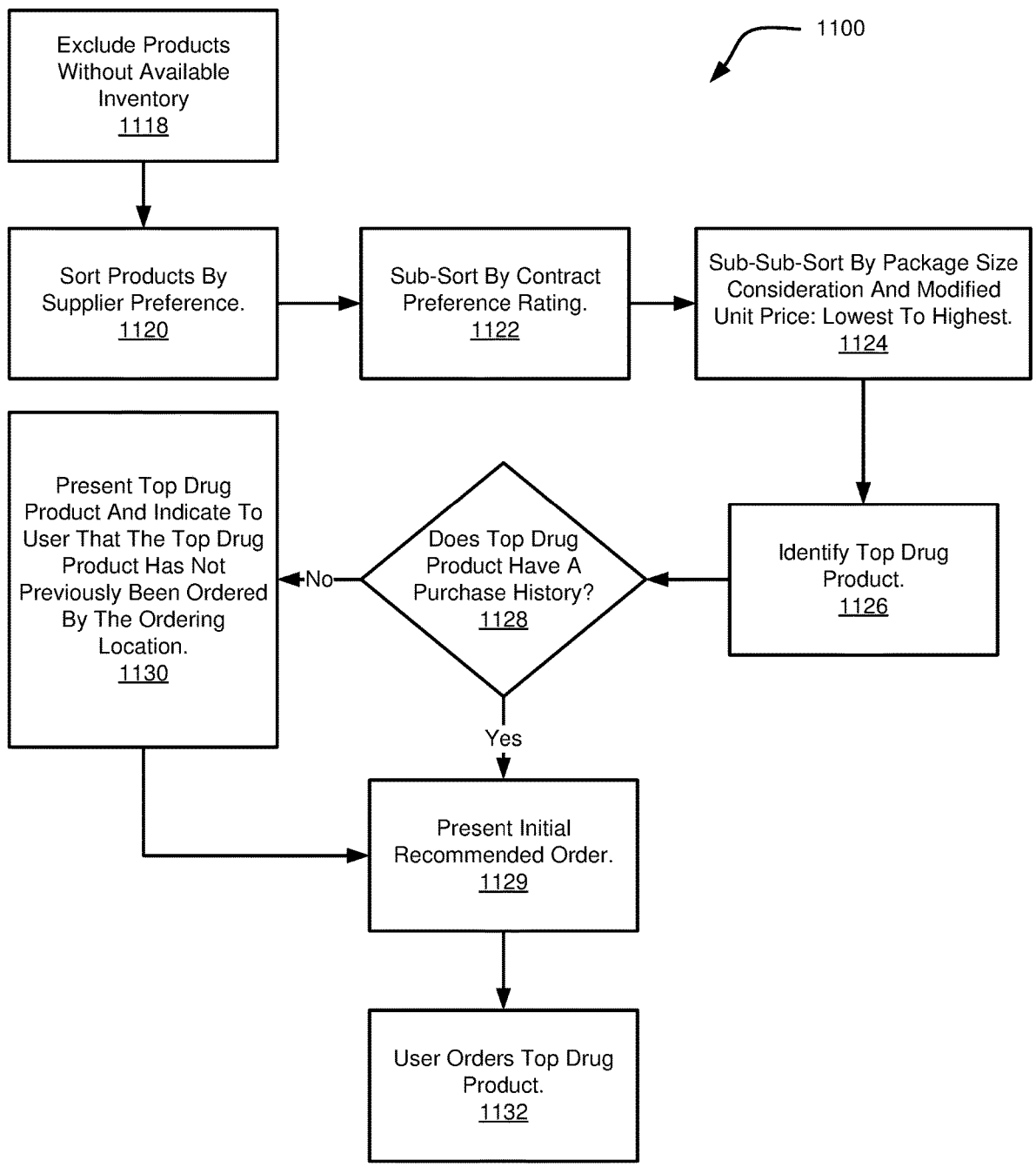

FIGS. 11A and 11B are schematic diagrams of a process 1100 for preparing a shopping cart to generate an initial recommended order. The process 1100 includes a pharmaceutical procurement server 104 preparing at 1102 an order in a shopping cart. The process 1100 includes excluding all drug products supplied by the ordering location at 1104. The process 1100 includes determining whether there is visibility into a supplier's 118 inventory at 1106. If there is visibility, the process 1100 includes determining whether there is a package type requirement for a medication at 1108. If there is a package type requirement, the process 1100 includes excluding undesired package types from search results at 1110. The process 1100 includes determining whether the desired drug products are available at 1112. If the desired drug products are not available, the process 1100 includes reintroducing excluded package types and notifying the user that the package type was reintroduced at 1114. The process 1100 includes again determining if drug products are available at 1116, and if drug products are available, excluding drug products without inventory at 1118. If it is determined that drug products are available at 1112, then the process 1100 includes excluding at 1118 drug products without available inventory.

FIG. 11B is a continuation of the process illustrated in FIG. 11A. After drug products without available inventory are excluded at 1118, the process 1100 includes sorting drug products by supplier preference at 1120. The process 1100 includes sub-sorting by contract preference rating at 1122. The process 1100 includes sub-sub-sorting by package size consideration and modified unit price: lowest to highest at 1124. The process 1100 includes identifying the top drug product at 1126 and determining whether the top drug product has a purchase history for the ordering location at 1128. If the top drug product does not have a purchase history, the process 1100 includes presenting the initial recommended order and indicating at 1130 to the user that the selected drug product has not previously been ordered by the ordering location and is therefore a new drug product. At this point, an initial recommended order may be presented to the user at 1129 and the user may process an order of the top drug product if desired at 1132. In an embodiment, the initial recommended order is presented to the user at 1129 at the same time the top drug product is presented to the user at 1130. If the top drug product does have a purchase history, the process 1100 includes presenting the initial recommended order at 1129, at which point the user can order the top drug product at 1132.

Figure 12:
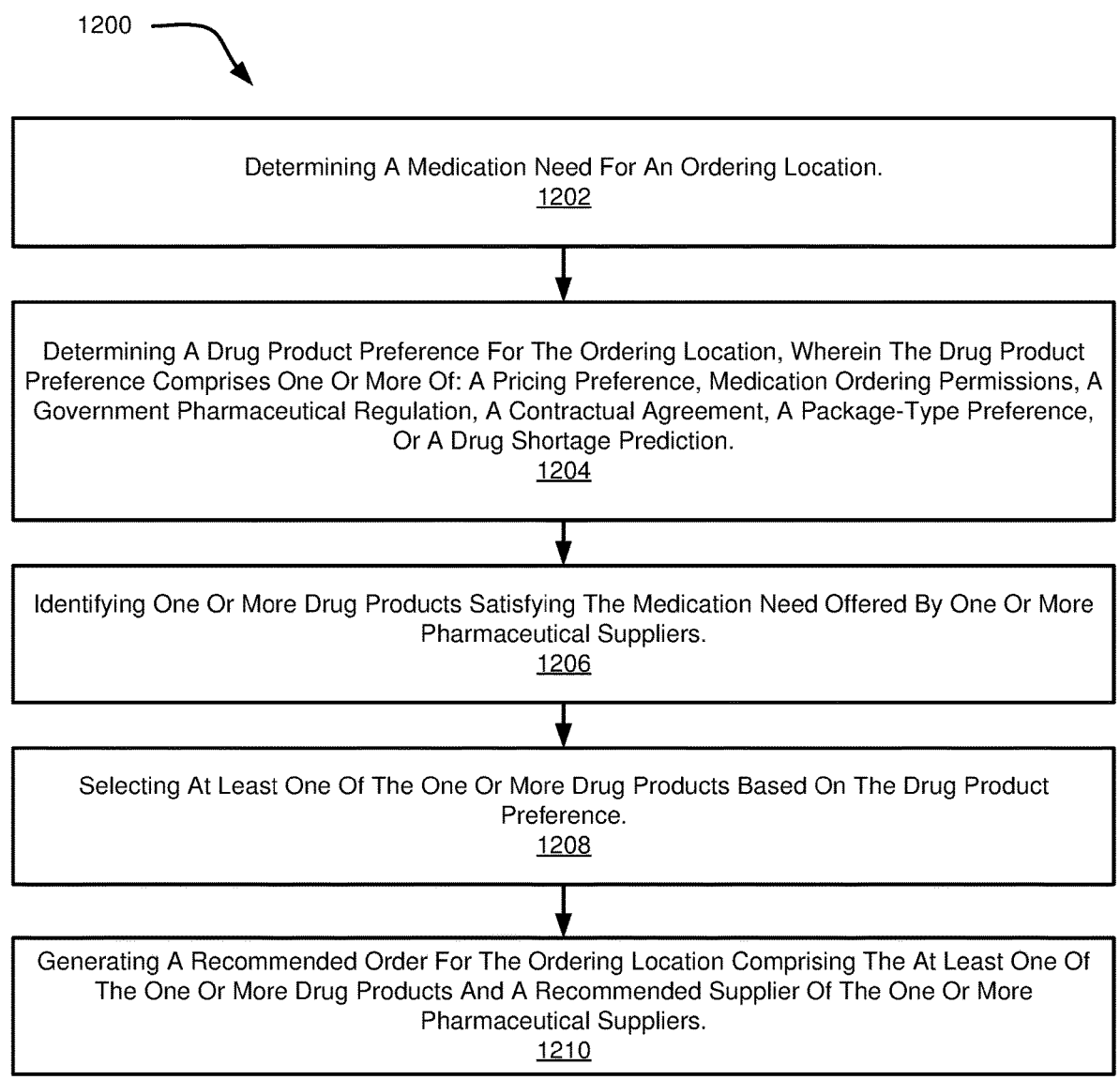
FIG. 12 is a schematic flow chart diagram of a method for generating a recommended pharmaceutical order based on parameters.

FIG. 12 is a schematic flow chart diagram of a method 1200 for generating a recommended pharmaceutical order. The method 1200 may be performed by a computing device such as the pharmaceutical procurement server 104 discussed herein. The pharmaceutical procurement server 104 may be in communication with one or more other computing resources such as the drug library 108, the active directory 110, the third-party administrator 112 server, the inventory management solution 114 server, the enterprise resource planning 116 server, the supplier 118, and/or a device 106 connected to the pharmaceutical procurement platform 102 by way of the network 120.

The method 1200 begins and a computing resource determines at 1202 a medication need for an ordering location. In an embodiment, the ordering location is a healthcare location of a health system. The medication need identifies a certain medication that the ordering location desires to purchase. In an embodiment, determining the medication need includes receiving a manual indication from a user at the ordering location that the ordering location desires to purchase the medication. The manual indication may additionally include an indication of how many units of the medication the ordering location wants to purchase. In an embodiment, determining the medication need includes receiving information from an inventory management solution 114 and automatically determining that the ordering location has low inventory of the medication.

The method 1200 continues and a computing resource determines at 1204 a drug product preference for the ordering location. The drug product preference may include one or more of a pricing preference of the ordering location, medication ordering permissions for the ordering location, a government pharmaceutical regulation, a contractual agreement with the ordering location or a health system over the ordering location, a package-type preference, or a drug shortage prediction. The drug product preferences may include a plurality of factors for selecting a certain drug product that falls under the umbrella of the medication that is needed by the ordering location. The pricing preference may include an indication that the ordering location wishes to prioritize the lowest-cost product, or products under a threshold cost, the lowest unit-dose cost, and so forth. The medication ordering permissions may indicate the medications and/or drug products that the ordering location, or an account associated with the ordering location, has permission to purchase, obtain, or dispense to patients.

The method 1200 continues and a computing resource identifies at 1206 one or more drug products satisfying the medication need offered by one or more pharmaceutical suppliers. The step of identifying the one or more products that satisfy the medication includes identifying drug products of the medication that is needed by the ordering location. A drug product is a specific item that is purchasable, and may indicate the manufacturer, wholesaler, supplier, package type, delivery method, brand name, generic status, and so forth.

The method 1200 continues and a computing resource selects at 1208 at least one of the one or more drug products based on the drug product preference. The step of selecting the at least one of the one or more drug products includes selecting a best drug product for the ordering location based on the drug product preferences for that ordering location. For example, this may include selecting a certain drug product because that drug product has rebate pricing or a favorable contractual relationship that makes the certain drug product more financially advantageous for the ordering location. For example, this may include selecting a certain drug product that is packaged in unit doses or bulk packaging according to the ordering location's preferences. For example, this may include selecting a certain drug product that is likely to experience a shortage in the future, and therefore it is advantageous to purchase the drug product now. The drug product preferences may be prioritized for the ordering location based on custom parameters. The method 1200 continues and a computing resource generates at 1210 a recommended order for the ordering location comprising the at least one of the one or more drug products and a recommended supplier of the one or more pharmaceutical suppliers.

Figure 13:
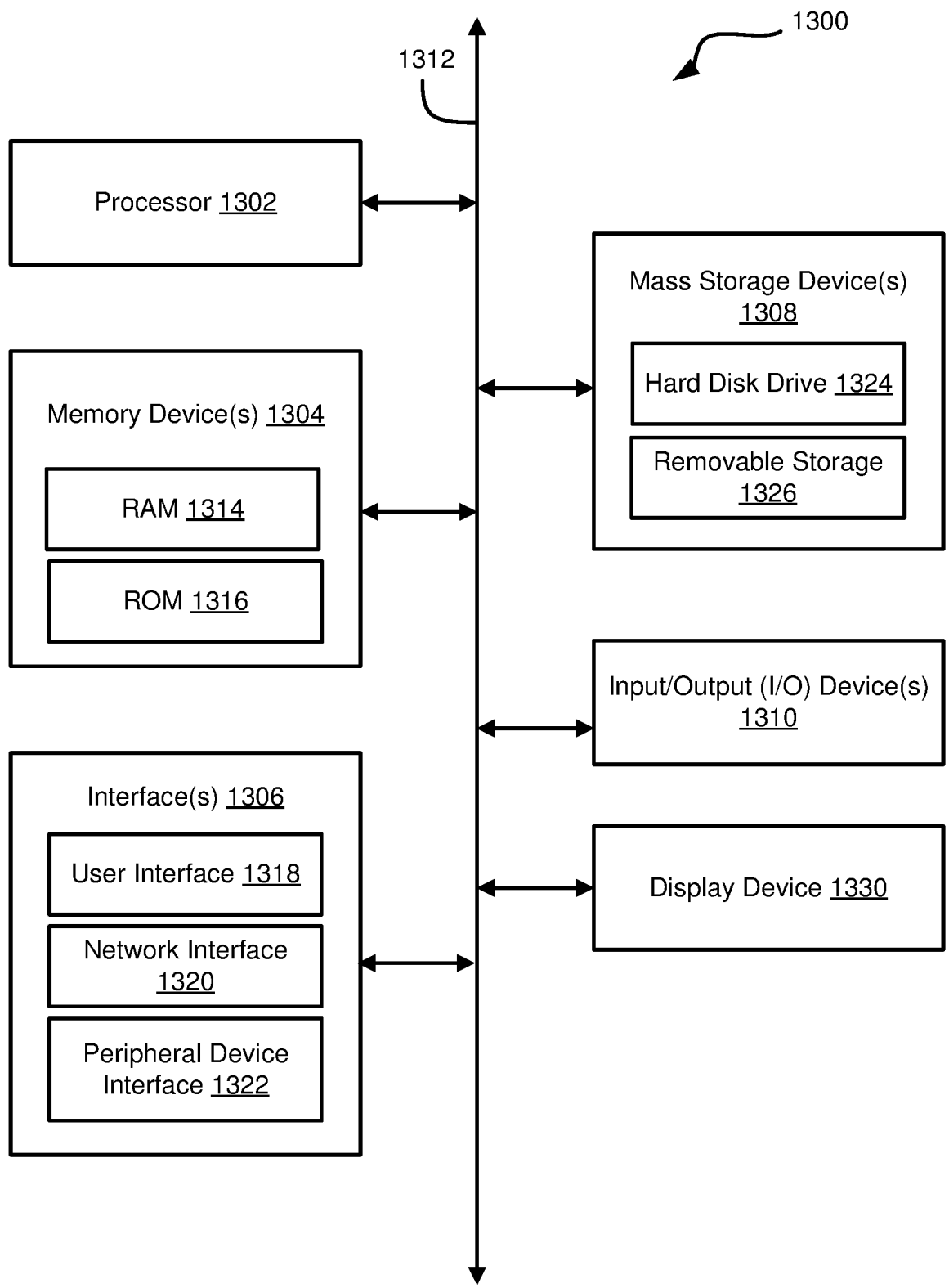
FIG. 13 is a schematic diagram illustrating components of an example computing device.

Referring now to FIG. 13, a block diagram of an example computing device 1300 is illustrated. Computing device 1300 may be used to perform various procedures, such as those discussed herein. Computing device 1300 can perform various monitoring functions as discussed herein, and can execute one or more application programs, such as the application programs or functionality described herein. Computing device 1300 can be any of a wide variety of computing devices, such as a desktop computer, in-dash computer, vehicle control system, a notebook computer, a server computer, a handheld computer, tablet computer and the like.

Computing device 1300 includes one or more processor(s) 1302, one or more memory device(s) 1304, one or more interface(s) 1306, one or more mass storage device(s) 1308, one or more Input/output (I/O) device(s) 1310, and a display device 1330 all of which are coupled to a bus 1312. Processor(s) 1302 include one or more processors or controllers that execute instructions stored in memory device(s) 1304 and/or mass storage device(s) 1308. Processor(s) 1302 may also include various types of computer-readable media, such as cache memory.

Memory device(s) 1304 include various computer-readable media, such as volatile memory (e.g., random access memory (RAM) 1314) and/or nonvolatile memory (e.g., read-only memory (ROM) 1316). Memory device(s) 1304 may also include rewritable ROM, such as Flash memory.

Mass storage device(s) 1308 include various computer readable media, such as magnetic tapes, magnetic disks, optical disks, solid-state memory (e.g., Flash memory), and so forth. As shown in FIG. 13, a particular mass storage device 1308 is a hard disk drive 1324. Various drives may also be included in mass storage device(s) 1308 to enable reading from and/or writing to the various computer readable media. Mass storage device(s) 1308 include removable media 1326 and/or non-removable media.

I/O device(s) 1310 include various devices that allow data and/or other information to be input to or retrieved from computing device 1300. Example I/O device(s) 1310 include cursor control devices, keyboards, keypads, microphones, monitors or other display devices, speakers, printers, network interface cards, modems, barcode scanners, and the like.

Display device 1330 includes any type of device capable of displaying information to one or more users of computing device 1300. Examples of display device 1330 include a monitor, display terminal, video projection device, and the like.

Interface(s) 1306 include various interfaces that allow computing device 1300 to interact with other systems, devices, or computing environments. Example interface(s) 1306 may include any number of different network interfaces 1320, such as interfaces to local area networks (LANs), wide area networks (WANs), wireless networks, and the Internet. Other interface(s) include user interface 1318 and peripheral device interface 1322. The interface(s) 1306 may also include one or more user interface elements 1318. The interface(s) 1306 may also include one or more peripheral interfaces 1322 such as interfaces for printers, pointing devices (mice, track pad, or any suitable user interface now known to those of ordinary skill in the field, or later discovered), keyboards, and the like.

Bus 1312 allows processor(s) 1302, memory device(s) 1304, interface(s) 1306, mass storage device(s) 1308, and I/O device(s) 1310 to communicate with one another, as well as other devices or components coupled to bus 1312. Bus 1312 represents one or more of several types of bus structures, such as a system bus, PCI bus, IEEE bus, USB bus, and so forth.

EXAMPLES

The following examples pertain to further embodiments.

Example 1 is a method. The method includes determining a medication need for an ordering location. The method includes determining a drug product preference for the ordering location, wherein the drug product preference comprises one or more of: a pricing preference, medication ordering permissions, a government pharmaceutical regulation, a contractual agreement, a package-type preference, or a drug shortage prediction. The method includes identifying one or more drug products satisfying the medication need offered by one or more pharmaceutical suppliers. The method includes selecting at least one of the one or more drug products based on the drug product preference. The method includes generating a recommended order for the ordering location comprising the at least one of the one or more drug products and a recommended supplier of the one or more pharmaceutical suppliers.

Example 2 is a method as in Example 1, wherein the drug product preference for the ordering location comprises one or more of: a formulary indicating a medication drug product group, wherein the medication drug product group is identified within a pharmaceutical procurement server comprising data obtained, parsed, and articulated from a drug library; a sub-formulary indicating a sub-level medication drug product group in which the ordering location has permission to purchase; the government pharmaceutical regulation; government pricing program requirements; the contractual agreement, wherein the contractual agreement comprises one or more contracts with one or more of: a pharmaceutical supplier, a pharmaceutical manufacturer, a healthcare location, or a health system; a health system regulation; the package-type preference; a package-type restriction; a unit-dose versus bulk-package preference; an indication of whether any of the one or more drug products is available internally in connection with the ordering location; or the drug shortage predictions and analysis.

Example 3 is a method as in any of Examples 1-2, further comprising: providing a drug product and/or medication drug product group to a neural network trained to predict a drug shortage based on a plurality of factors; receiving from the neural network a predicted shortage likelihood indicating one or more of whether there is currently a shortage of the drug product and/or medication drug product group or whether it is predicted there will be a shortage of the drug product and/or medication drug product group in the future; determining whether the predicted shortage likelihood meets a threshold; and in response to the predicted shortage likelihood meeting the threshold, generating a notification for a user comprising the predicted shortage likelihood.

Example 4 is a method as in any of Examples 1-3, wherein identifying the one or more drug products comprises identifying a plurality of drug products that satisfy the medication need and the drug product preference, and wherein the method further comprises sorting the plurality of drug products to generate sorted drug products based on one or more of: unit price; supplier preference for the ordering location; contract preference rating for the ordering location; or package size and/or package configuration preferences for the ordering location.

Example 5 is a method as in any of Examples 1-4, further comprising: identifying a top drug product based on the sorted drug products; determining whether the ordering location has previously purchased the top drug product; in response to determining the ordering location has previously purchased the top drug product, performing one or more of: automatically ordering the top drug product on behalf of the ordering location by communicating with a supplier for the top drug product; or facilitating a user-initiated transaction for ordering the top drug product using one or more of secure file transfer protocol (SFTP), an application program interface (API), a fax message, or an email; and in response to determining the ordering location has not previously purchased the top drug product, generating a message indicating the top drug product is a new drug product for the ordering location.

Example 6 is a method as in any of Examples 1-5, further comprising calculating business analytics feedback for the ordering location comprising recommendations for pharmaceutical procurement, wherein calculating the business analytics feedback comprises calculating based on one or more of: supplier contract terms with one or more potential pharmaceutical suppliers; supplier data received from the one or more potential pharmaceutical suppliers; pharmaceutical formularies; pharmaceutical availability; pharmaceutical pricing options, including contractual pricing options, rebate pricing options, and/or government pricing program options; or pharmaceutical packaging characteristics.

Example 7 is a method as in any of Examples 1-6, wherein selecting the at least one of the one or more drug products comprises selecting based on one or more of: supplier contract terms for the one or more drug products with the one or more suppliers; supplier data for the one or more drug products received from the one or more suppliers; current availability of the one or more drug products; pricing options for the one or more drug products, including contractual pricing options, rebate pricing options, and/or government pricing program options; or packaging characteristics for the one or more drug products in light of packaging preferences for the ordering location.

Example 8 is a method as in any of Examples 1-7, wherein: identifying the one or more drug products further comprises identifying based on data retrieved from a drug library database comprising a listing of possible pharmaceutical equivalents and further comprises an indication of generic and brand versions of drug products satisfying the medication need; and communicating with the one or more pharmaceutical suppliers comprises communicating by way of an application program interface and/or secure file transfer protocol.

Example 9 is a method as in any of Examples 1-8, further comprising: receiving a flat file from a third-party administrator by way of an SFTP, wherein the flat file comprises one or more of a third-party administrator identifier for the ordering location, a drug product identifier, or accumulation data for the ordering location; ingesting the accumulation data for the ordering location; articulating the accumulation data within a user interface accessible to a user at the ordering location. The method may additionally or alternatively include pinging an API of the third-party administrator with one or more of the third-party administrator identifier for the ordering location and drug product identifier; receiving a response from the third-party administrator by way of an application program interface (API), wherein the response comprises real-time accumulation data for the one or more drug products satisfying the medication need; ingesting the real-time accumulation data; and articulating the real-time accumulation data within the user interface accessible to the user at the ordering location.

Example 10 is a method as in any of Examples 1-9, further comprising: receiving an indication of pharmaceutical inventory quantities at the ordering location from an inventory management solution by way of an application program interface and/or a secure file transfer protocol; determining whether the pharmaceutical inventory quantities of the medication need satisfy a threshold quantity; and in response to the pharmaceutical inventory quantities of the medication need failing to satisfy the threshold quantity, generating the recommended order for the ordering location to comprise a sufficient quantity of the at least one of the one or more drug products to satisfy the threshold quantity.

Example 11 is a method as in any of Examples 1-10, further comprising: receiving an indication from a user as to a medication drug product group need, wherein the indication refers to the medication drug product group in a standard usable unit of measure; communicating with the one or more suppliers to identify a supplier with available inventory of a drug product from the medication drug product group; determining a package size for the supplier with the available inventory; and converting the indication from the user from the medication drug product group in the standard usable unit of measure to the drug product in the package size available from the supplier.

Example 12 is a method as in any of Examples 1-11, wherein the drug product preference is at least the pricing preference, and wherein the pricing preference comprises an indication that the ordering location desires a lowest cost drug product of the one or more drug products satisfying the medication need.

Example 13 is a method as in any of Examples 1-12, wherein the drug product preference is at least the pricing preference, and wherein the pricing preference comprises an indication that the ordering location desires a lowest unit cost drug product of the one or more drug products satisfying the medication need.

Example 14 is a method as in any of Examples 1-13, wherein the drug product preference is at least the pricing preference, and wherein the pricing preference comprises a threshold cost indicating that the ordering location does not wish to satisfy the medication need unless at least one drug product of the one or more drug products is priced less than the threshold cost.

Example 15 is a method as in any of Examples 1-14, wherein the drug product preference comprises the pricing preference and the method further comprises sorting each of the one or more drug products satisfying the medication need based on cost.

Example 16 is a method as in any of Examples 1-15, wherein generating the recommended order further comprises recommending the recommended supplier based on cost.

Example 17 is a method as in any of Examples 1-16, wherein generating the recommended order further comprises recommending the recommended supplier based on unit cost of the at least one drug product of the one or more drug products.

Example 18 is a method as in any of Examples 1-17, wherein the drug product preference comprises at least the contractual agreement, and wherein the contractual agreement comprises pricing information for the ordering location with a certain pharmaceutical supplier.

Example 19 is a method as in any of Examples 1-18, wherein the medication need defines a pharmaceutical equivalent drug product group.

Example 20 is a method as in any of Examples 1-19, wherein the medication need defines a therapeutically equivalent drug product group.

Example 21 is a method as in any of Examples 1-20, wherein the medication need defines a medical treatment plan, and wherein a plurality of drug products are used in the medical treatment plan.

Example 22 is a method as in any of Examples 1-21, wherein the medication need comprises inventory information for the ordering location indicating that the ordering location has a low supply of a certain medication, wherein the medication defines a pharmaceutical equivalent drug product group.

Example 23 is a method as in any of Examples 1-22, further comprising receiving inventory information for the ordering location from an inventory management solution; and determining whether current inventory of a certain medication at the ordering location satisfies a threshold inventory level.

Example 24 is a method as in any of Examples 1-23, further comprising, in response to determining the current inventory of the certain medication at the ordering location does not satisfy the threshold inventory level, determining the medication need for the ordering location, wherein the medication need comprises the certain medication.

Example 25 is a method as in any of Examples 1-24, wherein the medication ordering permissions comprise a listing of medications the ordering location does not have permission to order.

Example 26 is a method as in any of Examples 1-25, wherein the medication ordering permissions comprise a listing of medications the ordering location has permission to purchase.

Example 27 is a method as in any of Examples 1-26, wherein the ordering location comprises one or more of: a healthcare location with a pharmaceutical supply, a health system comprising a plurality of healthcare locations, an account associated with the healthcare location; or an account associated with the health system.

Example 28 is a method as in any of Examples 1-27, wherein the ordering location comprises an account associated with one or more of a healthcare location with a pharmaceutical supply or a health system, and wherein the account comprises unique drug product preferences relative to other accounts associated with the healthcare location or the health system.

Example 29 is a method as in any of Examples 1-28, wherein the contractual agreement comprises drug rebate information.

Example 30 is a method as in any of Examples 1-29, wherein the package-type preference comprises an indication of whether the ordering location prefers to fulfill the medication need with a bulk-packaged drug product or a unit-dosed drug product or any other package type.

Example 31 is a method as in any of Examples 1-30, wherein the medication need comprises a plurality of medications within a drug product kit, and wherein satisfying the medication need comprises identifying one or more drug products for each of the medications within the drug product kit.

Example 32 is a method as in any of Examples 1-31, wherein identifying the one or more drug products comprises communicating with at least one of the one or more pharmaceutical suppliers by way of one or more of an application program interface (API) of a secure file transfer protocol (SFTP).

Example 33 is a method as in any of Examples 1-32, wherein identifying the one or more drug products comprises referencing a listing of drug products offered by each of the one or more pharmaceutical suppliers.

Example 34 is a method as in any of Examples 1-33, wherein identifying the one or more drug products comprises receiving inventory information from at least one of the one or more pharmaceutical suppliers, and wherein the method further comprises identifying whether the one or more drug products are currently in-stock with the at least one of the one or more pharmaceutical suppliers.

Example 35 is a method as in any of Examples 1-34, wherein selecting the at least one of the one or more drug products based on the drug product preference comprises filtering the one or more drug products based on the package-type preference for the ordering location and sorting the one or more drug products based on cost, from lowest cost to highest cost.

Example 36 is a method as in any of Examples 1-35, wherein generating the recommended order comprising providing a recommendation on a certain drug product and a recommendation on a certain supplier from which to purchase the certain drug product.

Example 37 is a method as in any of Examples 1-36, wherein the one or more pharmaceutical suppliers comprise one or more of a pharmaceutical manufacturer, a pharmaceutical wholesaler, or an internal pharmaceutical supplier.

Example 38 is a method as in any of Examples 1-37, wherein the drug shortage prediction comprises a likelihood score that the medication is currently experiencing a shortage or will experience shortage in the future, and wherein the method further comprises receiving the drug shortage prediction from a neural network.

Example 39 is a method as in any of Examples 1-38, further comprising communicating with at least one of the one or more pharmaceutical suppliers to receive updated catalogue information indicating drug products offered by each of the at least one of the one or more pharmaceutical suppliers.

Example 40 is a method as in any of Examples 1-39, wherein the medication need comprises a medication the ordering location wishes to purchase, and wherein the method further comprises identifying pharmaceutical equivalents corresponding to the medication, wherein each of the pharmaceutical equivalents is a drug product.

Example 41 is a method as in any of Examples 1-40, wherein selecting the at least one of the one or more drug products based on the drug product preference comprises selecting based on lowest cost, and wherein determining lowest cost further comprises determining based on current cost for each of the at least one or more pharmaceutical suppliers, current drug rebates for each of the one or more pharmaceutical suppliers, and contractual agreements with each of the one or more pharmaceutical suppliers.

Example 42 is a method as in any of Examples 1-41, further comprising receiving an indication that a purchased drug product should be returned to a corresponding pharmaceutical supplier from which the purchased drug product was obtained.

Example 43 is a method as in any of Examples 1-42, further comprising, generating a label for returning the purchased drug product to the corresponding pharmaceutical supplier.

Example 44 is a method as in any of Examples 1-43, further comprising tracking a return status and a refund status of all purchased drug products that are being returned to corresponding pharmaceutical suppliers or have been returned to corresponding pharmaceutical suppliers.

Example 45 is non-transitory computer readable storage medium storing instructions for execution by one or more processors. The instructions include any of the method steps in Examples 1-44

Example 46 is a system. The system includes a server comprising one or more processors configurable to execute instructions stored in non-transitory computer readable storage media. The system includes a platform for facilitating pharmaceutical purchasing transactions, wherein the platform is executed by the one or more processors of the server. The instructions executed by the one or more processors of the server include any of the method steps in Examples 1-44.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium, which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, televisions, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. The terms "modules" and "components" are used in the names of certain components to reflect their implementation independence in software, hardware, circuitry, sensors, or the like. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein purposes of illustration and are not intended to be limiting. Embodiments of the present disclosure may be implemented in further types of devices, as would be known to persons skilled in the relevant art(s).

At least some embodiments of the disclosure have been directed to computer program drug products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method for pharmaceutical ordering and procurement for an ordering location, the method comprising:
   extracting drug product data for a plurality of drug products from a drug library, wherein each of the plurality of drug products is associated with a unique drug product identifier;
   parsing the drug product data into one or more tables of a database that is in communication with a network;
   extracting inventory data for the ordering location from an inventory management solution that manages drug inventory for the ordering location, wherein the inventory management solution comprises a robotic automated dispenser that dispenses at least a portion of the plurality of drug products at the ordering location;
   extracting current drug product pricing information from a plurality of pharmaceutical suppliers, wherein the current drug product pricing information is associated with the plurality of drug products;
   parsing the current drug product pricing information into the database;
   determining a medication need for procuring one or more of the plurality of drug products for the ordering location at least based on the inventory data, wherein the ordering location comprises one or more of a hospital, a clinic, a surgical center, an urgent care facility, a pharmacy, or a consolidated service center;
   identifying drug product preferences for the ordering location, wherein identifying the drug product preferences comprises:
      determining a pricing preference for the ordering location;
      identifying a formulary applicable to the ordering location, wherein the formulary identifies two or more of the plurality of drug products that are interchangeable, and wherein the formulary further identifies whether the ordering location must comply with a restriction associated with any of the plurality of drug products;
      determining whether a governmental pharmaceutical regulation applies to the ordering location; and
      identifying medication ordering permissions for the ordering location indicating which of the plurality of drug products the ordering location has permission to purchase or obtain;
   querying the one or more tables of the database to identify one or more of the plurality of drug products that satisfy the medication need, wherein each of the one or more of the plurality of drug products is associated with a unique drug product identifier;
   selecting a recommended drug product based on the drug product preferences for the ordering location, wherein the recommended drug product is associated with a delivery form, a release mechanism, and a package type that satisfies the medication need;
   calculating a recommended quantity of the recommended drug product to be procured for the ordering location based on an expected unit-dose disbursement of the recommended drug product by the ordering location; and
   selecting a recommended pharmaceutical supplier for acquiring at least a portion of the recommended quantity of the recommended drug product, wherein the recommended pharmaceutical supplier based at least in part on the current drug product pricing information extracted from the plurality of pharmaceutical suppliers; and
   generating a recommended pharmaceutical order for the ordering location, wherein the recommended pharmaceutical order comprises an indication of the recommended drug product, the recommended quantity, the delivery form, the release mechanism, the package type, and the recommended pharmaceutical supplier.

2. The method of claim 1, wherein the drug product preferences for the ordering location further comprise one or more of:
   a sub-formulary indicating a sub-level medication group in which the ordering location has permission to purchase;
   government pricing program requirements;
   a contractual agreement, wherein the contractual agreement comprises one or more contracts with one or more of: a pharmaceutical supplier, a pharmaceutical manufacturer, a healthcare location, or a health system;
   a health system regulation;
   a package-type restriction;
   a unit-dose versus bulk-package preference;
   an indication of whether any of the one or more of the plurality of drug products is available internally in connection with the ordering location; or
   analysis regarding a likelihood that a medication will experience a future drug shortage.

3. The method of claim 1, further comprising:
   providing a drug product associated with the medication need to an algorithm trained to calculate a drug shortage prediction for the drug product based on a plurality of factors;
   receiving an output from the algorithm indicating a likelihood of one or more of:
      a current shortage of the drug product associated with the medication need; or
      a future shortage of the drug product associated with the medication need;
   determining whether the likelihood of the drug shortage prediction meets a threshold; and
   in response to the likelihood of the drug shortage prediction meeting the threshold, generating a notification for a user comprising the drug shortage prediction for the drug product.

4. The method of claim 1, wherein selecting the recommended drug product comprises identifying two or more of the plurality of drug products that satisfy the medication need and the drug product preferences, and wherein the method further comprises sorting the two or more of the plurality of drug products to generate sorted drug products based on one or more of:
   unit price;
   supplier preference for the ordering location;
   contract preference rating for the ordering location; or
   package size and/or package configuration preferences for the ordering location.

5. The method of claim 4, further comprising:
   identifying a top drug product based on the sorted drug products;
   determining whether the ordering location has previously purchased the top drug product;
   in response to determining the ordering location has previously purchased the top drug product, performing one or more of:

automatically ordering the top drug product on behalf of the ordering location by communicating with a supplier for the top drug product; or facilitating a user-initiated transaction for ordering the top drug product using one or more of secure file transfer protocol (SFTP), an application program interface (API), a fax message, or an email; and in response to determining the ordering location has not previously purchased the top drug product, generating a message indicating the top drug product is a new drug product for the ordering location.

6. The method of claim 1, further comprising calculating business analytics feedback for the ordering location comprising recommendations for pharmaceutical procurement, and wherein calculating the business analytics feedback comprises calculating based on one or more of:

supplier contract terms with one or more of the plurality of pharmaceutical suppliers;

supplier data received from the one or more of the plurality of pharmaceutical suppliers;

pharmaceutical formularies;

pharmaceutical availability;

pharmaceutical pricing options comprising contractual pricing options, rebate pricing options, and/or government pricing program options; or pharmaceutical packaging characteristics.

7. The method of claim 1, wherein selecting the recommended drug product comprises selecting based on one or more of:

supplier contract terms received from one or more of the plurality of pharmaceutical suppliers for the recommended drug product;

supplier data received from the one or more of the plurality of pharmaceutical suppliers for the recommended drug product;

current availability of the recommended drug product;

pricing options for the recommended drug product comprising contractual pricing options, rebate pricing options, and/or government pricing program options; or packaging characteristics for the recommended drug product in light of packaging preferences for the ordering location.

8. The method of claim 1, wherein selecting the recommended drug product comprises selecting based on data retrieved from the drug library comprising a listing of possible pharmaceutical equivalents and an indication of generic and brand-name versions of two or more of the plurality of drug products all satisfying the medication need; and wherein extracting the current product pricing information comprises communicating with the plurality of pharmaceutical suppliers by way of an application program interface and/or secure file transfer protocol.

9. The method of claim 1, further comprising:

receiving an indication from a user to satisfy the medication need, wherein the medication need is indicated in a standard usable unit of measure;

communicating with one or more of the plurality of pharmaceutical suppliers to identify at least one pharmaceutical supplier with available inventory of the recommended drug product that satisfies the medication need;

determining a package size for the at least one pharmaceutical supplier with the available inventory of the recommended drug product; and converting the indication from the user referring to the medication need in the standard usable unit of measure to the package size available from the at least one pharmaceutical supplier.

10. The method of claim 1, further comprising:

receiving the inventory data for the ordering location from the inventory management solution by way of an application program interface and/or a secure file transfer protocol associated with a compute resource in communication with the robotic automated dispenser;

determining whether the inventory data for the ordering location indicates that the ordering location currently possess a threshold quantity of one or more drug products that satisfy the medication need; and in response to the ordering location not currently possessing the threshold quantity, generating the recommended pharmaceutical order for the ordering location to comprise a sufficient quantity of the recommended drug product to satisfy the threshold quantity.

11. Non-transitory computer readable storage medium storing instructions for execution by one or more processors, wherein the instructions are implemented to order and procure pharmaceuticals for an ordering location, and wherein the instructions comprise:

extracting drug product data for a plurality of drug products from a drug library, wherein each of the plurality of drug products is associated with a unique drug product identifier;

parsing the drug product data into one or more tables of a database that is in communication with a network;

extracting inventory data for the ordering location from an inventory management solution that manages drug inventory for the ordering location, wherein the inventory management solution comprises a robotic automated dispenser that dispenses at least a portion of the plurality of drug products at the ordering location;

extracting current drug product pricing information from a plurality of pharmaceutical suppliers, wherein the current drug product pricing information is associated with the plurality of drug products;

parsing the current drug product pricing information into the database;

determining a medication need for procuring one or more of the plurality of drug products for the ordering location at least based on the inventory data, wherein the ordering location comprises one or more of a hospital, a clinic, a surgical center, an urgent care facility, a pharmacy, or a consolidated service center;

identifying drug product preferences for the ordering location, wherein identifying the drug product preferences comprises:

determining a pricing preference for the ordering location;

identifying a formulary applicable to the ordering location, wherein the formulary identifies two or more of the plurality of drug products that are interchangeable, and wherein the formulary further identifies whether the ordering location must comply with a restriction associated with any of the plurality of drug products;

determining whether a governmental pharmaceutical regulation applies to the ordering location; and identifying medication ordering permissions for the ordering location indicating which of the plurality of drug products the ordering location has permission to purchase or obtain;

querying the one or more tables of the database to identify one or more of the plurality of drug products that satisfy the medication need, wherein each of the one or more of the plurality of drug products is associated with a unique drug product identifier;

selecting a recommended drug product based on the drug product preferences for the ordering location, wherein the recommended drug product is associated with a delivery form, a release mechanism, and a package type that satisfies the medication need;

calculating a recommended quantity of the recommended drug product to be procured for the ordering location based on an expected unit-dose disbursement of the recommended drug product by the ordering location; and selecting a recommended pharmaceutical supplier for acquiring at least a portion of the recommended quantity of the recommended drug product, wherein the recommended pharmaceutical supplier based at least in part on the current drug product pricing information extracted from the plurality of pharmaceutical suppliers; and generating a recommended pharmaceutical order for the ordering location, wherein the recommended pharmaceutical order comprises an indication of the recommended drug product, the recommended quantity, the delivery form, the release mechanism, the package type, and the recommended pharmaceutical supplier.

12. The non-transitory computer readable storage medium of claim 11, wherein the drug product preferences for the ordering location further comprise one or more of:
a sub-formulary indicating a sub-level medication group in which the ordering location has permission to purchase;
government pricing program requirements;
a contractual agreement comprising one or more contracts with one or more of: a pharmaceutical supplier, a pharmaceutical manufacturer, a healthcare location, or a health system;
a health system regulation;
a package-type restriction;
a unit-dose versus bulk-package preference;
an indication of whether any of the one or more of the plurality of drug products is available internally in connection with the ordering location; or
analysis regarding a likelihood that a medication will experience a future drug shortage.

13. The non-transitory computer readable storage medium of claim 11, wherein the instructions further comprise:
providing a drug product associated with the medication need to an algorithm trained to calculate a drug shortage prediction for the drug product based on a plurality of factors;
receiving an output from the algorithm indicating a likelihood of one or more of:
a current shortage of the drug product associated with the medication need; or
a future shortage of the drug product associated with the medication need;
determining whether the likelihood of the drug shortage prediction meets a threshold; and
in response to the likelihood of the drug shortage prediction meeting the threshold, generating a notification for a user comprising the drug shortage prediction for the drug product.

14. The non-transitory computer readable storage medium of claim 11, wherein the instructions are such that selecting the recommended drug product comprises identifying two or more of the plurality of drug products that satisfy the medication need and the drug product preferences, and wherein the method further comprises sorting the two or more of the plurality of drug products to generate sorted drug products based on one or more of:
unit price;
supplier preference for the ordering location;
contract preference rating for the ordering location; or
package size and/or package configuration preferences for the ordering location.

15. The non-transitory computer readable storage medium of claim 14, wherein the instructions further comprise:
identifying a top drug product based on the sorted drug products;
determining whether the ordering location has previously purchased the top drug product;
in response to determining the ordering location has previously purchased the top drug product, performing one or more of:
automatically ordering the top drug product on behalf of the ordering location by communicating with a supplier for the top drug product; or
facilitating a user-initiated transaction for ordering the top drug product using one or more of secure file transfer protocol (SFTP), an application program interface (API), a fax message, or an email; and
in response to determining the ordering location has not previously purchased the top drug product, generating a message indicating the top drug product is a new drug product for the ordering location.

16. The non-transitory computer readable storage medium of claim 11, wherein the instructions further comprise calculating business analytics feedback for the ordering location comprising recommendations for pharmaceutical procurement, and wherein calculating the business analytics feedback comprises calculating based on one or more of:
supplier contract terms with one or more of the plurality of pharmaceutical suppliers;
supplier data received from the one or more of the plurality of pharmaceutical suppliers;
pharmaceutical formularies;
pharmaceutical availability;
pharmaceutical pricing options comprising contractual pricing options, rebate pricing options, and/or government pricing program options; or
pharmaceutical packaging characteristics.

17. The non-transitory computer readable storage medium of claim 11, wherein the instructions are such that selecting the recommended drug product comprises selecting based on one or more of:
supplier contract terms received from one or more of the plurality of pharmaceutical suppliers for the recommended drug product;
supplier data received from the one or more of the plurality of pharmaceutical suppliers for the recommended drug product;
current availability of the recommended drug product;
pricing options for the recommended drug product comprising contractual pricing options, rebate pricing options, and/or government pricing program options; or
packaging characteristics for the recommended drug product in light of packaging preferences for the ordering location.

18. The non-transitory computer readable storage medium of claim 11, wherein the instructions are such that:

selecting the recommended drug product comprises selecting based on data retrieved from the drug library comprising a listing of possible pharmaceutical equivalents and an indication of generic and brand-name versions of two or more of the plurality of drug products all satisfying the medication need; and extracting the current product pricing information comprises communicating with the plurality of pharmaceutical suppliers by way of an application program interface and/or secure file transfer protocol.

19. The non-transitory computer readable storage medium of claim 11, wherein the instructions further comprise:

receiving an indication from a user to satisfy the medication need, wherein the medication need is indicated in a standard usable unit of measure;

communicating with one or more of the plurality of pharmaceutical suppliers to identify at least one pharmaceutical supplier with available inventory of the recommended drug product that satisfies the medication need;

determining a package size for the at least one pharmaceutical supplier with the available inventory of the recommended drug product; and converting the indication from the user referring to the medication need in the standard usable unit of measure to the package size available from the at least one pharmaceutical supplier.

20. The non-transitory computer readable storage medium of claim 11, wherein the instructions further comprise:

receiving the inventory data for the ordering location from the inventory management solution by way of an application program interface and/or a secure file transfer protocol associated with a compute resource in communication with the robotic automated dispenser;

determining whether the inventory data for the ordering location indicates that the ordering location currently possess a threshold quantity of one or more drug products that satisfy the medication need; and in response to the ordering location not currently possessing the threshold quantity, generating the recommended pharmaceutical order for the ordering location to comprise a sufficient quantity of the recommended drug product to satisfy the threshold quantity.

21. A system for ordering and procuring pharmaceuticals for an ordering location, the system comprising:

a server comprising one or more processors configurable to execute instructions stored in non-transitory computer readable storage media; and a platform for facilitating pharmaceutical purchasing transactions, wherein the platform is executed by the one or more processors of the server;

wherein the instructions executed by the one or more processors of the server comprises:

extracting drug product data for a plurality of drug products from a drug library, wherein each of the plurality of drug products is associated with a unique drug product identifier;

parsing the drug product data into one or more tables of a database that is in communication with a network;

extracting inventory data for the ordering location from an inventory management solution that manages drug inventory for the ordering location, wherein the inventory management solution comprises a robotic automated dispenser that dispenses at least a portion of the plurality of drug products at the ordering location;

extracting current drug product pricing information from a plurality of pharmaceutical suppliers, wherein the current drug product pricing information is associated with the plurality of drug products;

parsing the current drug product pricing information into the database;

determining a medication need for procuring one or more of the plurality of drug products for the ordering location at least based on the inventory data, wherein the ordering location comprises one or more of a hospital, a clinic, a surgical center, an urgent care facility, a pharmacy, or a consolidated service center;

identifying drug product preferences for the ordering location, wherein identifying the drug product preferences comprises:

determining a pricing preference for the ordering location;

identifying a formulary applicable to the ordering location, wherein the formulary identifies two or more of the plurality of drug products that are interchangeable, and wherein the formulary further identifies whether the ordering location must comply with a restriction associated with any of the plurality of drug products;

determining whether a governmental pharmaceutical regulation applies to the ordering location; and identifying medication ordering permissions for the ordering location indicating which of the plurality of drug products the ordering location has permission to purchase or obtain;

querying the one or more tables of the database to identify one or more of the plurality of drug products that satisfy the medication need, wherein each of the one or more of the plurality of drug products is associated with a unique drug product identifier;

selecting a recommended drug product based on the drug product preferences for the ordering location, wherein the recommended drug product is associated with a delivery form, a release mechanism, and a package type that satisfies the medication need;

calculating a recommended quantity of the recommended drug product to be procured for the ordering location based on an expected unit-dose disbursement of the recommended drug product by the ordering location; and selecting a recommended pharmaceutical supplier for acquiring at least a portion of the recommended quantity of the recommended drug product, wherein the recommended pharmaceutical supplier is selected based at least in part on the current drug product pricing information extracted from the plurality of pharmaceutical suppliers; and generating a recommended pharmaceutical order for the ordering location, wherein the recommended pharmaceutical order comprises an indication of the recommended drug product, the recommended quantity, the delivery form, the release mechanism, the package type, and the recommended pharmaceutical supplier.

22. The system of claim 21, wherein the drug product preferences for the ordering location further comprise one or more of:

a sub-formulary indicating a sub-level medication group in which the ordering location has permission to purchase;

government pricing program requirements;

a contractual agreement, wherein the contractual agreement comprises one or more contracts with one or more of: a pharmaceutical supplier, a pharmaceutical manufacturer, a healthcare location, or a health system;

a health system regulation;

a package-type restriction;

a unit-dose versus bulk-package preference;

an indication of whether any of the one or more of the plurality of drug products is available internally in connection with the ordering location; or analysis regarding a likelihood that a medication will experience a future drug shortage.

23. The system of claim 21, wherein the instructions further comprise:

providing a drug product associated with the medication need to an algorithm trained to calculate a drug shortage prediction for the drug product based on a plurality of factors;

receiving an output from the algorithm indicating a likelihood of one or more of:

a current shortage of the drug product associated with the medication need; or a future shortage of the drug product associated with the medication need;

determining whether the likelihood of the drug shortage prediction meets a threshold; and in response to the likelihood of the drug shortage prediction meeting the threshold, generating a notification for a user comprising the drug shortage prediction for the drug product.

24. The system of claim 21, wherein the instructions are such that selecting the recommended drug product comprises identifying two or more of the plurality of drug products that satisfy the medication need and the drug product preferences, and wherein the method further comprises sorting the two or more of the plurality of drug products to generate sorted drug products based on one or more of:

unit price;

supplier preference for the ordering location;

contract preference rating for the ordering location; or package size and/or package configuration preferences for the ordering location.

25. The system of claim 24, wherein the instructions further comprise:

identifying a top drug product based on the sorted drug products;

determining whether the ordering location has previously purchased the top drug product;

in response to determining the ordering location has previously purchased the top drug product, performing one or more of:

automatically ordering the top drug product on behalf of the ordering location by communicating with a supplier for the top drug product; or facilitating a user-initiated transaction for ordering the top drug product using one or more of secure file transfer protocol (SFTP), an application program interface (API), a fax message, or an email; and in response to determining the ordering location has not previously purchased the top drug product, generating a message indicating the top drug product is a new drug product for the ordering location.

26. The system of claim 21, wherein the instructions further comprise calculating business analytics feedback for the ordering location comprising recommendations for pharmaceutical procurement, and wherein calculating the business analytics feedback comprises calculating based on one or more of:

supplier contract terms with one or more of the plurality of pharmaceutical suppliers;

supplier data received from the one or more of the plurality of pharmaceutical suppliers;

pharmaceutical formularies;

pharmaceutical availability;

pharmaceutical pricing options comprising contractual pricing options, rebate pricing options, and/or government pricing program options; or pharmaceutical packaging characteristics.

27. The system of claim 21, wherein the instructions are such that selecting the recommended drug product comprises selecting based on one or more of:

supplier contract terms received from one or more of the plurality of pharmaceutical suppliers for the recommended drug product;

supplier data received from the one or more of the plurality of pharmaceutical suppliers for the recommended drug product;

current availability of the recommended drug product;

pricing options for the recommended drug product comprising contractual pricing options, rebate pricing options, and/or government pricing program options; or packaging characteristics for the recommended drug product in light of packaging preferences for the ordering location.

28. The system of claim 21, wherein the instructions are such that:

selecting the recommended drug product comprises selecting based on data retrieved from the drug library comprising a listing of possible pharmaceutical equivalents and an indication of generic and brand-name versions of two or more of the plurality of drug products all satisfying the medication need; and extracting the current product pricing information comprises communicating with the plurality of pharmaceutical suppliers by way of an application program interface and/or secure file transfer protocol.

29. The system of claim 21, wherein the instructions further comprise:

receiving an indication from a user to satisfy the medication need, wherein the medication need is indicated in a standard usable unit of measure;

communicating with one or more of the plurality of pharmaceutical suppliers to identify at least one pharmaceutical supplier with available inventory of the recommended drug product that satisfies the medication need;

determining a package size for the at least one pharmaceutical supplier with the available inventory of the recommended drug product; and converting the indication from the user referring to the medication need in the standard usable unit of measure to the package size available from the at least one pharmaceutical supplier.

30. The system of claim 21, wherein the instructions further comprise:

receiving the inventory data for the ordering location from the inventory management solution by way of an application program interface and/or a secure file transfer protocol associated with a compute resource in communication with the robotic automated dispenser;

determining whether the inventory data for the ordering location indicates that the ordering location currently possess a threshold quantity of one or more drug products that satisfy the medication need; and in response to the ordering location not currently possessing the threshold quantity, generating the recommended pharmaceutical order for the ordering location to comprise a sufficient quantity of the recommended drug product to satisfy the threshold quantity.

* * * * *